(12) United States Patent
Takahashi et al.

(10) Patent No.: US 8,257,656 B2
(45) Date of Patent: Sep. 4, 2012

(54) HEATER COIL FOR GAS SENSOR, DETECTING ELEMENT FOR GAS SENSOR, CATALYTIC COMBUSTION GAS SENSOR, AND MANUFACTURING METHOD OF CATALYTIC COMBUSTION GAS SENSOR

(75) Inventors: Ikuo Takahashi, Saitama (JP); Junji Satoh, Saitama (JP); Yoshirou Hirai, Saitama (JP)

(73) Assignee: Citizen Holdings Co., Ltd., Nishitokyo-shi (JP)

( * ) Notice: Subject to any disclaimer, the term of this patent is extended or adjusted under 35 U.S.C. 154(b) by 162 days.

(21) Appl. No.: 12/730,703

(22) Filed: Mar. 24, 2010

(65) Prior Publication Data
US 2010/0176094 A1    Jul. 15, 2010

Related U.S. Application Data

(62) Division of application No. 10/594,006, filed as application No. PCT/JP2005/005407 on Mar. 24, 2005, now Pat. No. 7,713,480.

(30) Foreign Application Priority Data

Mar. 30, 2004    (JP) .................................. 2004-101537
Mar. 30, 2004    (JP) .................................. 2004-101539

(51) Int. Cl.
*G01N 31/12*    (2006.01)
(52) U.S. Cl. .......................................................... 422/94
(58) Field of Classification Search .................... 422/94
See application file for complete search history.

(56) References Cited

U.S. PATENT DOCUMENTS

| | | | | |
|---|---|---|---|---|
| 2,258,836 A | * | 10/1941 | Willner | 313/333 |
| 2,703,833 A | * | 3/1955 | Vanvor | 338/28 |
| 3,725,720 A | * | 4/1973 | Petro et al. | 313/344 |
| 3,778,664 A | * | 12/1973 | Petro et al. | 313/344 |

(Continued)

FOREIGN PATENT DOCUMENTS

JP    52-116289    9/1977

(Continued)

OTHER PUBLICATIONS

Fuji Electric Co. Ltd. Japanese Utility Model Laid-Open Publication No. SHo 63-152553. Publication Date: Oct. 6, 1988. 17 pages.*

(Continued)

*Primary Examiner* — Bobby Ramdhanie
(74) *Attorney, Agent, or Firm* — Foley & Lardner LLP

(57) ABSTRACT

A lead portion (25) of a heater coil (22) is constituted of a single coil wound into a coil and a bead portion (24) is constituted of a double coil formed by further winding the single coil into a coil. By constituting a detecting element (2) by burying the bead portion (24) in a heat conductive layer (21) and adhering a catalyst layer (23) on the surface of the heat conductive layer (21), improvement of the gas sensitivity and the response speed of a catalytic combustion gas sensor is facilitated. Zero point variation is reduced by improving impact resistance. When both ends of the heater coil are fixed to electrode pins, both ends of the heater coil are welded to the electrode pins using a resistance welding method, etc., with a platinum wire, etc., wound on a primary core wire, and thereafter, the primary core wire is melted and eliminated while leaving the platinum wire, etc., by a wet etching process.

12 Claims, 13 Drawing Sheets

U.S. PATENT DOCUMENTS

| | | | | |
|---|---|---|---|---|
| 3,979,625 | A | * | 9/1976 | Roberts .................. 313/230 |
| 5,138,221 | A | | 8/1992 | Arato et al. |
| 6,465,949 | B1 | | 10/2002 | Miahara et al. |

FOREIGN PATENT DOCUMENTS

| JP | 59-137849 A | 8/1984 |
|---|---|---|
| JP | 2-059949 B2 | 11/1984 |
| JP | 61-082659 A | 4/1986 |
| JP | 63-152553 U | 10/1988 |
| JP | 3-037988 A | 2/1991 |
| JP | 3-162658 A | 7/1991 |
| JP | 10-050253 A | 2/1998 |
| JP | 2001-349891 A | 12/2001 |
| JP | 2003-121402 A | 4/2003 |

OTHER PUBLICATIONS

Kodama, S. JP2002-035930. Machine English Translation. Publication Date: Feb. 5, 2002. 11 pages.*

Tagawa et al. "Gas Sensing Element and Its Manufacturing Method." JP52116289 and Certified English Translation. 9 pages, Date: Oct. 2011.*

* cited by examiner

HEATER COIL FOR GAS SENSOR, DETECTING ELEMENT FOR GAS SENSOR, CATALYTIC COMBUSTION GAS SENSOR, AND MANUFACTURING METHOD OF CATALYTIC COMBUSTION GAS SENSOR

CROSS-REFERENCE TO RELATED APPLICATIONS

This application is a divisional of U.S. application Ser. No. 10/594,006, filed Sep. 25, 2006, now issued as U.S. Pat. No. 7,713,480, which is a National Stage of PCT/JP2005/005407, filed Mar. 24, 2005 which claims benefit of priority from the prior Japanese Application Nos. 2004-101539 and 2004-101537, filed on Mar. 30, 2004; the entire contents of all of which are incorporated herein by reference.

TECHNICAL FIELD

The present invention relates to a heater coil for a gas sensor, a detecting element for a gas sensor, a catalytic combustion gas sensor, and a manufacturing method of the catalytic combustion gas sensor.

BACKGROUND ART

Conventionally, a catalytic combustion gas sensor is known as a sensor for detecting combustible gases such as hydrogen gas, methane gas, etc. The catalytic combustion gas sensor detects presence of a combustible gas by heating, to a predetermined temperature, a detecting element formed by causing a heat conductive layer that covers a heater coil to carry a catalyst layer, burning the combustible gas by causing the combustible gas to contact the catalyst layer, and by outputting as variation of a voltage as variation of a resistance of the heater coil according to variation of the temperature caused by the combustion heat.

FIG. 18 is a cross-sectional view showing a configuration of a conventional detecting element. FIG. 19 is a front view showing the configuration of the conventional heater coil. As shown in FIG. 18, a conventional detecting element 1 is structured such that a heater coil 12 is buried in a heat conductive layer 11 and a catalyst layer 13 is adhered to the surface of the heat conductive layer 11. As shown in FIG. 19, for the conventional heater coil 12, the portion that is buried in the heat conductive layer 11 (hereinafter, "bead portion") is a single coil formed by winding a wire material into a coil (see, for example, Patent Document 1). Lead portions 15 extending respectively from the both ends of the bead portion 14 are not formed in a coil. In this specification, in the detecting element, a portion where the heat conductive layer and the catalyst layer covers the bead portion is referred to as "combusting portion".

In the catalytic combustion gas sensor, a Wheatstone bridge circuit is structure with the detecting element having the above structure, a compensating element having the same structured as this detecting element and carrying an inert oxide instead of catalyst, and two resistive elements. When the resistance of the heater coil varies due to combustion heat, the variation in resistance is output as variation in voltage from the Wheatstone bridge circuit (see, for example, Patent Document 2).

As a method of manufacturing the detecting element, a method of winding a resistive wire on a core wire; coating, in this state, with an insulating agent by electro-coating; performing heat firing on the insulating agent; thereafter, exposing a non-effective portion of the resistive wire; melting the core wire; and welding the core wire to an electrode pins, is known (see, for example, Patent Document 3). According to this method, when the detecting element is manufactured, the shape of the coiled portion of the resistive wire can be prevented from collapsing.

Patent Document 1: Japanese Patent Application Laid-Open Publication No. H3-162658 (FIG. 1)

Patent Document 2: Japanese Patent Application Laid-Open Publication No. H2-59949 (FIG. 1)

Patent Document 3: Japanese Patent Application Laid-Open Publication No. S52-116289

DISCLOSURE OF INVENTION

Problem to be Solved by the Invention

For catalytic combustion gas sensors, a larger amount of variation in voltage output from the Wheatstone bridge is preferable for the same gas concentrations. Large amount of variation in voltage means high concentration of the gas. If the winding number of winds of the coil in the bead portion of the heater coil is increased, the length of the portion (hereinafter, "effective length") that contributes to the resistance variation due to the combustion heat increases, and therefore, the sensitivity to gases is improved.

Moreover, for the catalytic combustion gas sensors, it is preferable for the voltage output from the Wheatstone bridge circuit to become stable in as short time as possible, for the same gas concentrations. Short time necessary for the output voltage to become stable means high response speed. To make the response speed higher, the wire material of the heater coil should be buried as longer as possible in the combusting portion such that the heater coil can efficiently receive the combustion heat and the variation of the resistance of the heater coil can be generated efficiently.

However, in either case, the bead portion of the heater coil becomes large, and accordingly, the amount of the heat conductive layer covering the bead portion and the amount of the catalyst layer increase. Therefore, the combusting portion becomes heavy. The detecting element is set in the sensor by being supported at the lead portions on both ends of the heater coil with the electrode pins for external connection. Therefore, if the combusting portion becomes heavy, the lead portions can not support the detecting element, and faults such as breakage of the lead portions, etc., are likely to occur.

Therefore, for the conventional catalytic combustion gas sensor, it is extremely difficult to facilitate improvement of the gas sensitivity and the improvement of the response speed without sacrificing the supporting ability of the detecting element in the lead portions of the heater coil. The conventional catalytic combustion gas sensor has no impact-absorbing property in the lead portions of the heater coil thereof. Therefore, when an impact is externally applied on the sensor, the impact is concentrated on the combusting portion with almost no alleviation of the impact. Therefore, detachment of the catalyst layer is likely to occur, and the zero point already adjusted is significantly varied.

Instead of the conventional heater coil of which only the portion that is buried in the combusting portion is formed in a coil, the inventors of the present invention propose a use of a coiled coil formed by further winding, into a coil, a portion of a coil wire that is formed by winding a wire material into a coil, as the heater coil. According to this proposal, even though the external shape dimensions are the same as those of the conventional heater coil, the actual length of the wire material forming the proposed heater coil is longer than that of the conventional heater coil. Therefore, the resistance of the heater coil becomes larger and the gas sensitivity becomes higher. The coiled-coil portion of the proposed heater coil is buried in the combusting portion. Thus, the length of the wire material in the combusting portion becomes longer than that of the conventional heater coil, and therefore, the resistance variation of the heater coil is generated more efficiently, and the response speed becomes higher.

However, in the heater coil formed with a coiled coil, the portions to be welded to the electrode pins are already coil-shaped. Therefore, it has been learned that a new problem as follows arise in the method of welding the core wire after the melting thereof as disclosed in the above Patent Document 3. For example, the wound portion of the coil is often crushed due to carelessness when the heater coil is handled after melting the core wire. During welding, in the welded portion, the wound portion of the heater coil is crushed irregularly or the coil shape is distorted. Thus, the heater coil is partially shorted, and therefore, the dispersion of the resistance values of heater coils becomes large in a lot. Because the core wire has been melted, a portion in which the core wire had been arranged, that is, the interior of the coil becomes a cavity. Therefore, the welded portion itself is unstable and the sufficient bonding strength can not be obtained.

The present invention has been achieved in view of the above problems, and it is the object of the present invention to provide a gas sensor heater coil, a gas sensor detecting element, and a catalytic combustion gas sensor that can facilitate improvement of the gas sensitivity without sacrificing the supporting ability of the detecting element in the lead portions of the heater coil, or to provide a gas sensor heater coil, a gas sensor detecting element, and a catalytic combustion gas sensor that can facilitate the improvement of the response speed without sacrificing the supporting ability of the detecting element in the lead portions of the heater coil. Moreover, it is an object of the present invention to provide a gas sensor heater coil, a gas sensor detecting element, and a catalytic combustion gas sensor that can reduce variation of the zero point when an impact is applied on the sensor.

Furthermore, it is an object of the present invention to provide a manufacturing method of a catalytic combustion gas sensor according to which the heater coil can be easily handled without collapsing the shape of the wound portion of the heater coil of which at least both ends are respectively wound in a coil-shape. Furthermore, it is an object of the present invention to provide a manufacturing method of a catalytic combustion gas sensor according to which the dispersion of the resistance values of heater coils each of which at least both ends are respectively wound in a coil-shape can be made small. Moreover, it is an object of the present invention to provide a manufacturing method of a catalytic combustion gas sensor in which the bonding strength between the heater coil of which at least both ends are respectively wound in a coil and the electrode pins can be improved.

Means for Solving Problem

To solve the above problems, and to achieve the objects, a heater coil for a gas sensor according to one example is a heater coil used in a catalytic combustion gas sensor, and includes a bead portion of which an electrical characteristic value is varied by combustion heat generated when a gas is burned; and lead portions extending from both ends of the bead portion. The bead portion is constituted of an n-fold coil formed by winding a plain wire into a coil, the plain wire formed with an (n−1)-fold coil that is wound into a coil, where n is an integer equal to or larger than two.

By manufacturing a detecting element using this heater coil, even when the size of the combusting portion of the detecting element is same as that of the conventional combusting portion, the effective length of the bead portion buried in the combusting portion is longer than that of a bead portion that is constituted of a conventional single coil. Therefore, the resistance of the heater coil becomes larger and, therefore, the gas sensitivity of the catalytic combustion gas sensor employing this heater coil becomes higher. The response speed of the catalytic combustion gas sensor employing this heater coil is higher because the heater coil receives more combustion heat and causes resistance variation more efficiently. The weight of the combusting portion is almost same as that of the conventional combusting portion because the size of the combusting portion may be almost same as that of the conventional combusting portion. Therefore, by employing this heater coil, improvement of the gas sensitivity and improvement of the response speed can be facilitated without sacrificing the supporting ability of the detecting element in the lead portions.

In another example, the lead portions are constituted of an (n−1)-fold coil.

In another example, the lead portions of a heater coil for a gas sensor are constituted of an (n−1)-fold coil.

In the catalytic combustion gas sensor employing this heater coil, an impact imposed externally is absorbed by the spring elasticity of the lead portions because the lead portions respectively have the same constitution as that of a coil spring. Therefore, the impact transmitted to the combusting portion is alleviated. Therefore, detachment of the catalyst layer, etc., does not tend to occur and significant variation of the zero point of the catalytic combustion gas sensor caused by the impact can be suppressed.

In the heater for a gas sensor according to another example, a wire diameter of a non-coiled raw wire that is a starting material is equal to or larger than 1 μm and equal to or smaller than 100 μm.

Because the wire diameter of the raw wire is equal to or larger than 1 μm, manufacture of a heater coil of which the bead portion consists of a multi-fold-wound coil is easy. Because the wire diameter of the raw wire is equal to or smaller than 100 μm, by employing this heater coil, a detecting element having a size suitable for employing in the catalytic combustion gas sensor can be obtained.

In the heater coil for a gas sensor according to another example, a wire diameter of a non-coiled raw wire that is a starting material is equal to or larger than 10 μm and equal to or smaller than 50 μm.

By employing this heater coil, a power source circuit having an appropriate voltage-current value can be used as a power source circuit for driving a control circuit of the catalytic combustion gas sensor. Using the appropriate power source circuit is important because the catalyst layer can be maintained at an appropriate operating temperature when the catalytic combustion gas sensor is operated.

In the heater coil for a gas sensor according to another example, a wire diameter of a non-coiled raw wire that is a starting material is equal to or larger than 20 μm and equal to or smaller than 30 μm.

Because a detecting element having the combusting portion weighing approximately 1 mg can be obtained by employing this heater coil, the lead portions of the heater coil can sufficiently support the detecting element. The catalytic combustion gas sensor employing this heater coil has an improved shock resistance thereof. Because the bead portion of the heater coil can be more densely buried in the combusting portion of the detecting element by employing this heater coil, the heater coil can receive more combusting heat. Thus, the resistance variation of the heater coil can be generated more efficiently. Therefore, the response speed is higher in the catalytic combustion gas sensor employing this heater coil. Because the resistance of the heater coil becomes larger, the power source voltage can be set higher. Therefore, the gas sensitivity becomes higher in the catalytic combustion gas sensor employing this heater coil.

Moreover, when the wire diameter of the raw wire is smaller than 20 μm, the yield obtained when this heater coils are manufactured is degraded. However, the heater coil can be manufactured easily because the wire diameter of the raw wire is equal to or larger than 20 μm. That is, the heater coil can be manufactured without degrading the yield and, by employing the heater coil, the gas sensitivity and the response property of the catalytic combustion gas sensor can be more improved. Based on the above, the optimal wire diameter of the raw wire is equal to or larger than 20 μm and equal to or smaller than 30 μm considering the balance between the gas sensitivity and the response property of the catalytic combustion gas sensor and the easiness of the manufacture of the heater coil.

In the heater coil for a gas sensor according to another example, a winding diameter of an m-fold coil is equal to or larger than 0.5 times and equal to or smaller than 20 times as large as a diameter of a core metal used for winding into a coil when the m-fold coil is manufactured, where m is an integer equal to or larger than one and equal to or smaller than n.

Because the combusting portion of the detecting element is prevented from being heavy by employing this heater coil, the lead portions of the heater coil can sufficiently support the detecting element. In contrast, when a heater coil having an m-fold-wound coil having a winding diameter exceeding 20 times as large as the diameter of the core metal is used, the amount of the heat conductive layer filled in the internal space of the coil of the bead portion is increased and the combusting portion becomes heavy. Therefore, the supporting performance of the lead portions against the detecting element is degraded and a disadvantage arises that the shock-resisting performance of the catalytic combustion gas sensor may be degraded out of the practically-permitted range.

In the heater coil for a gas sensor according to another example, a winding diameter of an m-fold coil is equal to or larger than 1 time and equal to or smaller than 10 times as large as a diameter of a core metal used for winding into a coil when the m-fold coil is manufactured, where m is an integer equal to or larger than one and equal to or smaller than n.

The heater coils can be obtained with a high yield because the shape stability of the m-fold-wound coils after the winding process is excellent. The supporting performance of the lead portions against the detecting element can be stably obtained. However, even when the winding diameter of the m-layer-winding coil is equal to or smaller than 20 times as large as the diameter of the core metal, if the winding diameter exceeds 10 times as large as the diameter of the core metal, the shape stability of the m-fold-wound coil after the winding process is degraded to some extent.

In the heater coil for a gas sensor according to another example, the number of turns of the n-fold coil is equal to or larger than 1 and equal to or smaller than 30.

Because the combusting portion of the detecting element is prevented from being heavy by employing this heater coil, the detecting element can be sufficiently supported by the lead portions of the heater coil. When a heater coil having the n-fold-wound coil having the number of turns of 30 is employed, the combusting portion becomes heavy and the detecting element can not be supported stably by the lead portions of the heater coil.

In the heater coil for a gas sensor according to another example, length of a gap between a wound portion of a k-th turn and a wound portion of a (k+1)-th turn in the n-fold coil is equal to or larger than 0.5 times and equal to or smaller than 10 times as large as a diameter of the plain wire formed by the (n−1)-fold coil, where k is an integer equal to or larger than one.

In the catalytic combustion gas sensor employing this heater coil, a sufficiently high response property can be obtained. When a detecting element is manufactured using this heater coil, the wound portion of the k-th turn and the wound portion of the (k+1)-th turn in the n-fold-wound coil can be prevented from shorting with each other as well as the catalyst layer can be formed by filling the heat conductive layer in the internal space of the coil of the bead portion. In contrast, for a heater coil having the gap, that is shorter than half the length of the diameter of the wire, between the wound portion of the k-th turn and the wound portion of the (k+1)-th turn, adjacent wound wires may contact each other and may short with each other. When the length of the gap exceeds a length 10 times as large as the diameter of the wire, because the gap between the wound portions is too wide, the heat conductive layer can not be fully filled in the internal space of the coil of the bead portion and, therefore, the catalyst layer can not be formed.

The heater coil for a gas sensor according to another example is constituted of a wire material made of platinum according to any one of the examples above. The heater coil for a gas sensor according to another example is constituted of a wire material made of platinum based alloy according to any one of the examples above.

A heater coil for a gas sensor according to another example is used in a catalytic combustion gas sensor, and includes a bead portion of which an electrical characteristic value is varied by combustion heat generated when a gas is burned; and lead portions extending from both ends of the bead portion. The lead portions are wound into a coil.

In the catalytic combustion gas sensor employing this heater coil, an impact imposed externally is absorbed by the spring elasticity of the lead portions because the lead portions have the same constitution as that of a coil spring. Therefore, the impact transmitted to the combusting portion of the detecting element is alleviated. Therefore, detachment of the catalyst layer, etc., does not tend to occur and significant variation of the zero point of the catalytic combustion gas sensor caused by the impact can be suppressed.

Moreover, to solve the above problems and to achieve the objects, a detecting element for a gas sensor according to another example is used in a catalytic combustion gas sensor, and includes a heater coil including a bead portion of which an electrical characteristic value is varied by combustion heat generated when a gas is burned; and lead portions extending from both ends of the bead portion; a heat conductive layer covering the bead portion; and a catalyst layer adhered on a surface of the heat conductive layer. The bead portion is constituted of an n-fold coil formed by winding a plain wire into a coil, the plain wire formed with an (n−1)-fold coil that is wound into a coil, where n is an integer equal to or larger than two.

Even when the size of the combusting portion of the detecting element is same as that of the conventional combusting portion, the effective length of the bead portion buried in the combusting portion is longer than that obtained when the bead portion is constituted of the conventional single coil. Therefore, in the catalytic combustion gas sensor employing this detecting element, the gas sensitivity is higher because the resistance of the heater coil becomes larger. The response speed of the catalytic combustion gas sensor employing this detecting element is higher because the heater coil receives more combustion heat and generates resistance variation efficiently. The weight of the combusting portion is almost same as that of the conventional combusting portion because the size of the combusting portion may be almost same as that of the conventional combusting portion. Therefore, improvement of the gas sensitivity and improvement of the response speed of the catalytic combustion gas sensor can be facilitated without sacrificing the supporting ability of the detecting element in the lead portions.

In the detecting element for a gas sensor according to another example, the lead portions of the heater coil is constituted of an (n−1)-fold coil.

In the catalytic combustion gas sensor employing this detecting element, an impact imposed externally is absorbed by the spring elasticity of the lead portions because the lead portions of the heater coil has the same constitution as that of a coil spring. Therefore, the impact transmitted to the combusting portion is alleviated. Therefore, detachment of the catalyst layer, etc., does not tend to occur and significant variation of the zero point of the catalytic combustion gas sensor caused by the impact can be suppressed.

In the detecting element for a gas sensor according to another example, a wire diameter of a non-coiled raw wire that is a starting material of the heater coil is equal to or larger than 1 µm and equal to or smaller than 100 µm.

Because the wire diameter of the raw wire of the heater coil is equal to or larger than 1 µm, a heater coil of which the bead portion consists of a multi-fold-wound coil can be easily manufactured. Therefore, manufacture of the detecting element is easy. Because the wire diameter of the raw wire of the heater coil is equal to or smaller than 100 µm, a detecting element having a size suitable for employing in the catalytic combustion gas sensor can be obtained.

In the detecting element for a gas sensor according to another example, a wire diameter of a non-coiled raw wire that is a starting material of the heater coil is equal to or larger than 10 µm and equal to or smaller than 50 µm.

By employing this detecting element, a power source circuit having an appropriate voltage-current value can be used as a power source circuit for driving a control circuit of the catalytic combustion gas sensor. Using the appropriate power source circuit is important because the catalyst layer can be maintained at an appropriate operating temperature when the catalytic combustion gas sensor is operated.

In the detecting element for a gas sensor according to another example, a wire diameter of a non-coiled raw wire that is a starting material of the heater coil is equal to or larger than 20 µm and equal to or smaller than 30 µm.

Because the weight of the combusting portion can be made approximately 1 mg, the lead portions of the heater coil can sufficiently support the detecting element. The catalytic combustion gas sensor employing this detecting element has an improved shock resistance. Because the bead portion of the heater coil can be more densely buried in the combusting portion, the heater coil can receive more combusting heat. Thus, the resistance variation of the heater coil can be generated more efficiently. Therefore, the response speed is higher in the catalytic combustion gas sensor employing this detecting element. Because the resistance of the heater coil becomes larger, the power source voltage can be set higher. Therefore, the gas sensitivity becomes higher in the catalytic combustion gas sensor employing this detecting element.

Furthermore, when the wire diameter of the raw wire of the heater coil is smaller than 20 µm, the yield obtained when the heater coil is manufactured is degraded. However, the heater coil can be manufactured easily because the wire diameter of the raw wire of the heater coil is equal to or larger than 20 µm. Therefore, the detecting element can be obtained at a high yield. That is, the detecting element can be manufactured without degrading the yield and, by employing the detecting element manufactured, the gas sensitivity and the response property of the catalytic combustion gas sensor can be more improved. Based on the above, the optimal wire diameter of the raw wire of the heater coil is equal to or larger than 20 µm and equal to or smaller than 30 µm considering the balance between the gas sensitivity and the response property of the catalytic combustion gas sensor and the easiness of the manufacture of the heater coil.

In the detecting element for a gas sensor according to another example, a winding diameter of an m-fold coil of the heater coil is equal to or larger than 0.5 times and equal to or smaller than 20 times as large as a diameter of a core metal used for winding into a coil when the m-fold coil is manufactured, where m is an integer equal to or larger than one and equal to or smaller than n.

Because the combusting portion is prevented from being heavy, the lead portions of the heater coil can sufficiently support the detecting element. In contrast, when a heater coil having an m-fold-wound coil having a winding diameter exceeding 20 times as large as the diameter of the core metal is used, the amount of the heat conductive layer filled in the internal space of the coil of the bead portion is increased and the combusting portion becomes heavy. Therefore, the supporting performance of the lead portions against the detecting element is degraded and a disadvantage arises that the shock-resisting performance of the catalytic combustion gas sensor may be degraded out of the practically-permitted range.

The detecting element for a gas sensor according to another example, a winding diameter of an m-fold coil of the heater coil is equal to or larger than 1 times and equal to or smaller than 10 times as large as a diameter of a core metal used for winding into a coil when the m-fold coil is manufactured, where m is an integer equal to or larger than one and equal to or smaller than n.

When the heater coil is manufactured, the heater coil can be obtained with a high yield because the shape stability of the m-fold-wound coil after the winding process is excellent. Therefore, the detecting element can be obtained at a high yield. The supporting performance of the lead portions against the detecting element can be stably obtained. However, even when the winding diameter of the m-fold-winding coil is equal to or smaller than 20 times as large as the diameter of the core metal, if the winding diameter exceeds 10 times as large as the diameter of the core metal, the shape stability of the m-fold-wound coil after the winding process is degraded to some extent.

In the detecting element for a gas sensor according to another example, the number of turns of the n-fold coil of the heater coil is equal to or larger than 1 and equal to or smaller than 30.

Because the combusting portion is prevented from being heavy, the detecting element can be sufficiently supported by the lead portions of the heater coil. When a heater coil having the n-fold-wound coil having the number of turns of 30 is employed, the combusting portion becomes heavy and the detecting element can not be supported stably by the lead portions of the heater coil.

In the detecting element for a gas sensor according to another example, length of a gap between a wound portion of a k-th turn and a wound portion of a (k+1)-th turn in the n-fold coil is equal to or larger than 0.5 times and equal to or smaller than 10 times as large as a diameter of the plain wire formed by the (n−1)-fold coil, where k is an integer equal to or larger than one.

In the catalytic combustion gas sensor employing this detecting element, a response property that is sufficiently high can be obtained. When the detecting element is manufactured, the wound portion of the k-th turn and the wound portion of the (k+1)-th turn in the n-fold-wound coil can be prevented from shorting with each other as well as the catalyst layer can be formed by filling the heat conductive layer in the internal space of the coil of the bead portion. In contrast, when a heater coil having the gap, that is shorter than half the length of the diameter of the wire, between the wound portion of the k-th turn and the wound portion of the (k+1)-th turn is used, adjacent wound wires may contact each other and may short with each other. When the length of the gap exceeds a length 10 times as large as the diameter of the wire, because the gap between the wound portions is too wide, the heat conductive layer can not be fully filled in the internal space of the coil of the bead portion and, therefore, the catalyst layer can not be formed.

In the detecting element for a gas sensor according to another example, the heater coil according to any one of examples above is constituted of a wire material of platinum. In the detecting element for a gas sensor according to another example, the heater coil according to any one of examples above is constituted of a wire material of platinum based alloy.

A detecting element for a gas sensor according to another example is used in a catalytic combustion gas sensor, and includes a heater coil including a bead portion of which an electrical characteristic value is varied by combustion heat generated when a gas is burned; and lead portions extending from both ends of the bead portion; a heat conductive layer covering the bead portion; and a catalyst layer adhered on a surface of the heat conductive layer. The lead portions of the heater coil are wound in a coil.

In the catalytic combustion gas sensor employing this detecting element, an impact imposed externally is absorbed by the spring elasticity of the lead portions because the lead portions of the heater coil respectively have the same constitution as that of a coil spring. Therefore, the impact transmitted to the combusting portion is alleviated. Therefore, detachment of the catalyst layer, etc., does not tend to occur and significant variation of the zero point of the catalytic combustion gas sensor caused by the impact can be suppressed.

Moreover, to solve the above problems and to achieve the objects, a catalytic combustion gas sensor according to another example includes a detecting element including a heater coil including a bead portion of which an electrical characteristic value is varied by combustion heat generated when a gas is burned; and lead portions extending from both ends of the bead portion; a heat conductive layer covering the bead portion; and a catalyst layer adhered on a surface of the heat conductive layer, wherein the bead portion is constituted of an n-fold coil formed by winding a plain wire into a coil, the plain wire formed with an (n−1)-fold coil that is wound into a coil, where n is an integer equal to or larger than two; a compensating element connected in series with the detecting element, and including another heater coil having a same configuration as that of the heater coil; a first resistive element; a second resistive element connected in series with the first resistive element; and a power source that applies a DC voltage respectively across both ends of a series-connected body formed with the detecting element and the compensating element, and a series-connected body formed with the first resistive element and the second resistive element. The detecting element, the compensating element, the first resistive element, and the second resistive element form a Wheatstone bridge circuit, and a voltage across, a connecting node between the detecting element and the compensating element, and a connecting node between the first resistive element and the second resistive element is output from the Wheatstone bridge circuit.

According to an example, even when the size of the combusting portion of the detecting element is same as that of the conventional combusting portion, the effective length of the bead portion buried in the combusting portion is longer than that obtained when the bead portion is constituted of the conventional single-fold-wound coil. Therefore, the gas sensitivity is higher because the resistance of the heater coil becomes larger. The response speed is higher because the heater coil receives more combustion heat and generates resistance variation efficiently. The weight of the combusting portion is almost same as that of the conventional combusting portion because the size of the combusting portion may be almost same as that of the conventional combusting portion. Therefore, improvement of the gas sensitivity and improvement of the response speed can be facilitated without sacrificing the supporting ability of the detecting element in the lead portions.

In the catalytic combustion gas sensor according to another example, the lead portions of the heater coil is constituted of an (n−1)-fold coil.

An impact imposed externally is absorbed by the spring elasticity of the lead portions because the lead portions of the heater coil respectively have the same constitution as that of a coil spring. Therefore, the impact transmitted to the combusting portion is alleviated. Therefore, detachment of the catalyst layer, etc., does not tend to occur and significant variation of the zero point caused by the impact can be suppressed.

In the catalytic combustion gas sensor according to another example, a wire diameter of a non-coiled raw wire that is a starting material of the heater coil is equal to or larger than 1 µm and equal to or smaller than 100 µm.

Because the wire diameter of the raw wire of the heater coil is equal to or larger than 1 µm, a heater coil of which the bead portion consists of a multi-fold-wound coil can be easily manufactured. Therefore, manufacture of the detecting element is easy and, therefore, manufacture of the catalytic combustion gas sensor is easy. Because the wire diameter of the raw wire of the heater coil is equal to or smaller than 100 µm, the catalytic combustion gas sensor having a detecting element of a suitable size can be obtained.

In the catalytic combustion gas sensor according to another example, a wire diameter of a non-coiled raw wire that is a starting material of the heater coil is equal to or larger than 10 µm and equal to or smaller than 50 µm.

According to this example, a power source circuit having an appropriate voltage-current value can be used as a power source circuit for driving a control circuit of the catalytic combustion gas sensor. Using the appropriate power source circuit is important because the catalyst layer can be maintained at an appropriate operating temperature when the catalytic combustion gas sensor is operated.

In the catalytic combustion gas sensor according to another example, a wire diameter of a non-coiled raw wire that is a starting material of the heater coil is equal to or larger than 20 µm and equal to or smaller than 30 µm.

Because the weight of the combusting portion can be made approximately 1 mg, the lead portions of the heater coil can sufficiently support the detecting element. The catalytic combustion gas sensor employing this heater coil has an improved shock resistance. Because the bead portion of the heater coil can be more densely buried in the combusting portion, the heater coil can receive more combusting heat. Thus, the resistance variation of the heater coil can be generated more efficiently. Therefore, the response speed is higher. Because the resistance of the heater coil becomes larger, the power source voltage can be set higher. Therefore, the gas sensitivity becomes higher.

Moreover, when the wire diameter of the raw wire of the heater coil is smaller than 20 μm, the yield obtained when the heater coil is manufactured is degraded. However, the heater coil can be manufactured easily because the wire diameter of the raw wire of the heater coil is equal to or larger than 20 μm. Therefore, the catalytic combustion gas sensor can be obtained at a high yield. That is, the catalytic combustion gas sensor can be manufactured without degrading the yield and the gas sensitivity and the response property can be more improved. Based on the above, the optimal wire diameter of the raw wire of the heater coil is equal to or larger than 20 μm and equal to or smaller than 30 μm considering the balance between, the gas sensitivity and the response property, and the easiness of the manufacture of the heater coil.

In the catalytic combustion gas sensor according to another example, a winding diameter of an m-fold coil of the heater coil is equal to or larger than 0.5 times and equal to or smaller than 20 times as large as a diameter of a core metal used for winding into a coil when the m-fold coil is manufactured, where m is an integer equal to or larger than one and equal to or smaller than n.

Because the combusting portion of the detecting element is prevented from being heavy, the lead portions of the heater coil can sufficiently support the detecting element. In contrast, when a heater coil having an m-fold-wound coil having a winding diameter exceeding 20 times as large as the diameter of the core metal is used, the amount of the heat conductive layer filled in the internal space of the coil of the bead portion is increased and the combusting portion becomes heavy. Therefore, the supporting performance of the lead portions against the detecting element is degraded and a disadvantage arises that the shock-resisting performance may be degraded out of the practically-permitted range.

In the catalytic combustion gas sensor according to another example, a winding diameter of an m-fold coil of the heater coil is equal to or larger than 1 times and equal to or smaller than 10 times as large as a diameter of a core metal used for winding into a coil when the m-fold coil is manufactured, where m is an integer equal to or larger than one and equal to or smaller than n.

When the heater coil is manufactured, the heater coil can be obtained with a high yield because the shape stability of the m-fold-wound coil after the winding process is excellent. Therefore, the catalytic combustion gas sensor can be obtained at a high yield. The supporting performance of the lead portions against the detecting element can be stably obtained. However, even when the winding diameter of the m-layer-winding coil is equal to or smaller than 20 times as large as the diameter of the core metal, if the winding diameter exceeds 10 times as large as the diameter of the core metal, the shape stability of the m-fold-wound coil after the winding process is degraded to some extent.

In the catalytic combustion gas sensor according to another example, the number of turns of the n-fold coil of the heater coil is equal to or larger than 1 and equal to or smaller than 30.

Because the combusting portion is prevented from being heavy, the detecting element can be sufficiently supported by the lead portions of the heater coil. When a heater coil having the n-fold-wound coil having the number of turns of 30 is employed, the combusting portion becomes heavy and the detecting element can not be supported stably by the lead portions of the heater coil.

In the catalytic combustion gas sensor according to another example, length of a gap between a wound portion of a k-th turn and a wound portion of a (k+1)-th turn in the n-fold coil is equal to or larger than 0.5 times and equal to or smaller than 10 times as large as a diameter of the plain wire formed by the (n−1)-fold coil, where k is an integer equal to or larger than one.

A sufficiently high response property can be obtained. When the detecting element is manufactured, the wound portion of the k-th turn and the wound portion of the (k+1)-th turn in the n-fold-wound coil can be prevented from shorting with each other as well as the catalyst layer can be formed by filling the heat conductive layer in the internal space of the coil of the bead portion. In contrast, when a heater coil having the gap, that is shorter than half the length of the diameter of the wire, between the wound portion of the k-th turn and the wound portion of the (k+1)-th turn is used, adjacent wound wires may contact each other and may short with each other. When the length of the gap exceeds a length 10 times as large as the diameter of the wire, because the gap between the wound portions is too wide, the heat conductive layer can not be fully filled in the internal space of the coil of the bead portion and, therefore, the catalyst layer can not be formed.

In the catalytic combustion gas sensor according to another example, the heater coil according to any one of the examples above is constituted of a wire material of platinum. In the catalytic combustion gas sensor according to another example, the heater coil according to any one of the examples above is constituted of a wire material of platinum based alloy.

A catalytic combustion gas sensor according to another example includes a detecting element including a heater coil including a bead portion of which an electrical characteristic value is varied by combustion heat generated when a gas is burned; and lead portions extending from both ends of the bead portion; a heat conductive layer covering the bead portion; and a catalyst layer adhered on a surface of the heat conductive layer, wherein the lead portions are wound into a coil; a compensating element connected in series with the detecting element, and including another heater coil having a same configuration as that of the heater coil; a first resistive element; a second resistive element connected in series with the first resistive element; and a power source that applies a DC voltage respectively across both ends of a series-connected body formed with the detecting element and the compensating element, and a series-connected body formed with the first resistive element and the second resistive element. The detecting element, the compensating element, the first resistive element, and the second resistive element form a Wheatstone bridge circuit, and a voltage across, a connecting node between the detecting element and the compensating element, and a connecting node between the first resistive element and the second resistive element is output from the Wheatstone bridge circuit.

An impact imposed externally is absorbed by the spring elasticity of the lead portions because the lead portions of the heater coil respectively have the same constitution as that of a coil spring. Therefore, the impact transmitted to the combusting portion of the detecting element is alleviated. Therefore, detachment of the catalyst layer, etc., does not tend to occur and significant variation of the zero point caused by the impact can be suppressed.

A catalytic combustion gas sensor according to another example detects presence of a combustible gas based on variation of an electrical characteristic value of a heater coil obtained when the characteristic value is varied by combustion heat generated by burning of a gas that the gas sensor has contacted. The catalytic combustion gas sensor includes a heater coil of which at least both ends are wound into a coil; electrodes respectively welded to coiled portions on the both sides of the heater coil; and a sintered body covering a portion of the heater coil. An alloy layer including at least one metal element constituting the electrodes at a higher percentage than a composing percentage thereof in the electrodes is present in a bonding boundary between the heater coil and the electrodes.

A catalytic combustion gas sensor according to an example detects presence of a combustible gas based on variation of an electrical characteristic value of a heater coil obtained when the characteristic value is varied by combustion heat generated by burning of a gas that the gas sensor has contacted, the catalytic combustion gas sensor includes a heater coil of which at least both ends are wound into a coil; electrodes respectively welded to coiled portions on both sides of the heater coil; and a sintered body covering a portion of the heater coil. An alloy layer including at least one metal element constituting the electrodes at a higher percentage than a composing percentage thereof in the electrodes is present in a bonding boundary between the heater coil and the electrodes, and a core wire made from a metal element included in the alloy at a higher percentage than that in the electrodes is provided on an inner side of a coiled portion of the heater coil only in a welded portion of the heater coil and the electrodes.

According to an example, the alloy layer including the metal element that constitutes the electrodes at a higher composing percentage than the composing percentage of the metal element in the electrodes (hereinafter, "rich layer") is present in the bonding interface between the heater coil and the electrodes. Therefore, high bonding strength can be obtained. The rich layer is formed by alloying of the metal material constituting the core wire with the metal material of the electrodes due to welding of the core wire, that is constituted of at least one metal element that constitutes the electrodes, with the ends of the heater coil wound thereon, with the electrodes. Therefore, the core wire is present inside the wound portions on the ends of the heater coil during the welding. Therefore, the wound portion can be prevented from being crushed due to carelessness in the handling during the welding. Because the wound portion of the heater coil can be prevented from being crushed irregularly or the coil shape can be prevented from being distorted in the welded portion during the welding, the dispersion of the resistance values of heater coils can be made small.

In the catalytic combustion gas sensor according to another example, the metal element included in the alloy at a higher percentage than that in the electrodes has stronger ionization tendency than the metal constituting the heater coil.

Because the core wire can be melted by etching after the core wire with the ends of the heater coils wound thereon has been welded with the electrodes, the core wire can be easily eliminated by removing the rich layer. Even when the heater coil is constituted of a coiled coil described later, the core wire can be easily eliminated after the welding.

In the catalytic combustion gas sensor according to another example, the heater coil is made from any one of platinum and platinum alloy, the electrodes are made of alloy including nickel, and the metal element included in the alloy at a higher percentage than that in the electrodes is nickel.

The core wire is made of nickel and, therefore, the core wire can be easily melted remaining the heater coil because nickel is more basic metal than platinum or platinum alloy.

The catalytic combustion gas sensor according to another example, at least a part of the portion covered with the sintered body is a coiled coil formed by further winding a coiled wire into a coil, the coiled wire formed by winding a wire material into a coil.

Because the wire material constituting the heater coil becomes longer, the resistance of the heater coil becomes larger and, therefore, the gas sensitivity becomes higher. Because a longer length of the wire material constituting the heater coil is buried in the sintered body, the resistance variation of the heater coil can be efficiently generated and, therefore, the response speed becomes higher.

A catalytic combustion gas sensor according to another example detects presence of a combustible gas based on variation of an electrical characteristic value of a heater coil obtained when the characteristic value is varied by combustion heat generated by burning of a gas that the gas sensor has contacted. The catalytic combustion gas sensor includes a heater coil of which at least both ends are wound into a coil; electrodes respectively welded to coiled portions on both sides of the heater coil; and a sintered body covering a portion of the heater coil. An alloy layer generated by alloying a metal element not included in any of the heater coil and the electrodes and at least one metal element constituting the electrodes is present in a bonding boundary between the heater coil and the electrodes.

A catalytic combustion gas sensor according to another example detects presence of a combustible gas based on variation of an electrical characteristic value of a heater coil obtained when the characteristic value is varied by combustion heat generated by burning of a gas that the gas sensor has contacted. The catalytic combustion gas sensor includes a heater coil of which at least both ends are wound into a coil; electrodes respectively welded to coiled portions on both sides of the heater coil; and a sintered body covering a portion of the heater coil. An alloy layer generated by alloying a metal element not included in any of the heater coil and the electrodes and at least one metal element constituting the electrodes is present in the bonding boundary between the heater coil and the electrodes, and a core wire made from a metal element included in the alloy layer but not included in any of the heater coil and the electrodes is provided on an inner side of the coiled portion of the heater coil only at a welded portion of the heater coil and the electrodes.

According to an example, the alloy layer generated by alloying of the metal element not included in any of the heater coil and the electrodes and at least one metal element constituting the electrodes is present in the bonding interface between the heater coil and the electrodes. Therefore, high bonding strength can be obtained. The alloy layer is formed by alloying of the metal material constituting the core wire with the metal material of the electrodes due to welding of the core wire, that is constituted of a metal element that is not included in any of the heater coil and the electrodes, with the ends of the heater coil wound thereon, with the electrodes. Therefore, the core wire is present inside the wound portion on the ends of the heater coil during the welding. Therefore, the wound portion can be prevented from being crushed due to carelessness in the handling during the welding. Because the wound portion of the heater coil can be prevented from being crushed irregularly or the coil shape can be prevented from being distorted in the welded portion during the welding, the dispersion of the resistance values of heater coils can be made small.

The catalytic combustion gas sensor according to another example, the metal element included in the alloy layer but not included in any of the heater coil and the electrodes has stronger ionization tendency than the metal constituting the heater coil.

According to this example, because the core wire can be melted by etching after the core wire with the ends of the heater coils wound thereon has been welded with the electrodes, the core wire can be easily eliminated by removing the alloy layer. Even when the heater coil is constituted of a coiled coil described later, the core wire can be easily eliminated after the welding.

In the catalytic combustion gas sensor according to another example, at least a part of the portion covered with the sintered body is a coiled coil formed by further winding a coiled wire into a coil, the coiled wire formed by winding a wire material into a coil.

According to this example, because the wire material constituting the heater coil becomes longer, the resistance of the heater coil becomes larger and, therefore, the gas sensitivity becomes higher. Because a longer length of the wire material constituting the heater coil is buried in the sintered body, the resistance variation of the heater coil can be efficiently generated and, therefore, the response speed is made higher.

Moreover, to solve the above problems and to achieve the objects, a manufacturing method according to another example is for manufacturing a catalytic combustion gas sensor that detects presence of a combustible gas based on variation of an electrical characteristic value of a heater coil obtained when the characteristic value is varied by combustion heat generated by burning of a gas that the gas sensor has contacted, and includes a coil manufacturing step of manufacturing a heater coil of which at least both ends thereof respectively have been formed into a coil by being wound on a core wire; a welding step of welding coiled portions on both ends of the heater coil respectively to electrode in a state in which the coiled portions are wound on a core wire; a core wire eliminating step of eliminating the core wire; and a sintered-body coating step of coating a portion of the heater coil with a sintered body, the portion from which the core wire is eliminated.

A manufacturing method according to another example is for manufacturing a catalytic combustion gas sensor that detects presence of a combustible gas based on variation of an electrical characteristic value of a heater coil obtained when the characteristic value is varied by combustion heat generated by burning of a gas that the gas sensor has contacted. The manufacturing method includes a coil manufacturing step of manufacturing a heater coil of which at least both ends thereof respectively have been formed into a coil by being wound on a core wire; a welding step of welding coiled portions on both ends of the heater coil respectively to electrode in a state in which the coiled portions are wound on a core wire; a core wire eliminating step of eliminating the core wire except welded portions of the heater coil and the electrodes; and a sintered-body coating step of coating at least a part of a portion of the heater coil with a sintered body, the portion at which the core wire is not present.

Because the core wire is present inside the wound portion on the ends of the heater coil during the welding, the wound portion can be prevented from being crushed due to carelessness in the handling during the welding. Because the wound portion of the heater coil can be prevented from being crushed irregularly or the coil shape can be prevented from being distorted in the welded portion during the welding, the dispersion of the resistance values of heater coils can be made small. Because the alloy layer is generated in the bonding interface between the heater coil and the electrodes, high bonding strength can be obtained.

In the manufacturing method of a catalytic combustion gas sensor according to another example, at the welding step any one of a resistance welding method, a laser welding method, and a thermo-compression bonding method is performed while the ends wound on the core wire of the heater coil is kept pressed to the electrodes.

According to this example, because the wound portion of the heater coil can be easily prevented from being crushed irregularly in the welded portion, the dispersion of the resistance values of heater coils can be made small.

The manufacturing method of a catalytic combustion gas sensor according to another example, the core wire is made from a metal material that is more basic metal than the constituting material of the heater coil, and only the core wire is eliminated by etching at the core wire eliminating step.

According to this example, the core wire can be melted by etching after the core wire with the ends of the heater coils wound thereon has been welded with the electrodes. Even when the heater coil is constituted of a coiled coil described later, the core wire can be easily eliminated after the welding.

In the manufacturing method of a catalytic combustion gas sensor according to this example, the core wire is made of nickel, the heater coil is made of platinum or platinum alloy, and the core wire is eliminated using an etching liquid for nickel at the core wire eliminating step in the invention according to any of the examples above.

According to this example, the core wire can be easily melted by etching remaining the heater coil because nickel is more basic metal than platinum or platinum alloy.

In the catalytic combustion gas sensor according to another example, at the coil manufacturing step at least a part of the portion of the heater coil covered with the sintered body is formed into a coiled coil that is formed by further winding a coiled wire into a coil, the coiled wire wound on the core wire.

According to this example, because the wire material constituting the heater coil becomes longer, the resistance of the heater coil becomes larger and, therefore, the catalytic combustion gas sensor having higher gas sensitivity can be obtained. Because a longer length of the wire material constituting the heater coil is buried in the sintered body, the resistance variation of the heater coil can be efficiently generated and, therefore, the sensor having a high response speed can be obtained.

In the manufacturing method of a catalytic combustion gas sensor according to another example, the core wire also acts as brazing material to bond the heater coil and the electrodes.

According to this example, sufficiently high bonding strength can be obtained even though welding is not executed using newly prepared brazing filler metal.

Effect of the Invention

The gas sensor heater coil, the gas sensor detecting element, and the catalytic combustion gas sensor according to the present invention exert an effect that the catalytic combustion gas sensor that has high gas sensibility can be obtained, an effect that the catalytic combustion gas sensor that has a high response speed can be obtained, and an effect that the catalytic combustion gas sensor that has small zero point variation caused by an impact can be obtained.

The manufacturing method of the catalytic combustion gas sensor according to the present invention exerts an effect that the catalytic combustion gas sensor that has the heater coil of with at least both ends are respectively wound in coils and for which the dispersion of the resistance values of the heater coils is small can be obtained, an effect that the catalytic combustion gas sensor that has the heater coil with at least both ends thereof respectively wound in coils and that has high bonding strength between the heater coil and the electrode pins can be obtained, and an effect that handling of the heater coil with at least both ends thereof respectively wound in coils is easy when the catalytic combustion gas sensor is manufactured.

Figure 1:
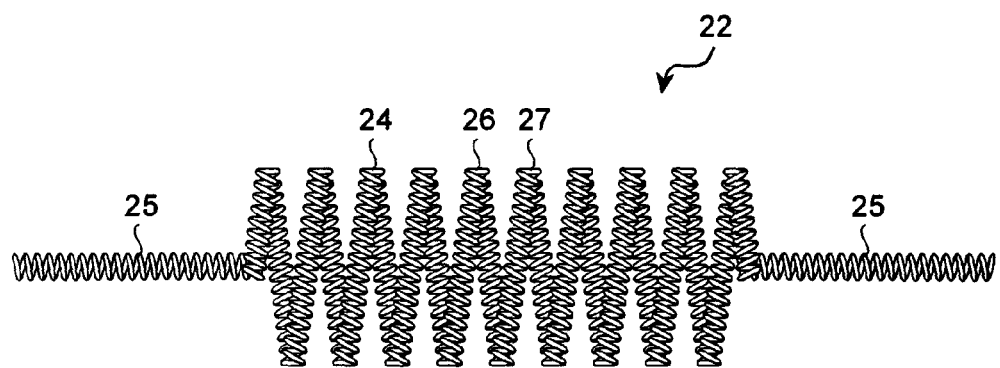
FIG. 1 is a front view showing a structure of a heater coil according to an embodiment of the present invention.

| EXPLANATIONS OF LETTERS OR NUMERALS | |
|---|---|
| 2 | Detecting element |
| 4 | Compensating element |
| 5 | Catalytic combustion gas sensor |
| 21 | Heat conductive layer |
| 22 | Heater coil |
| 23 | Catalyst layer |
| 24 | Bead portion |
| 25 | Lead portion |

| EXPLANATIONS OF LETTERS OR NUMERALS | |
|---|---|
| 26, 27 | Wound portion |
| 32, 33 | Electrode pin |
| 51 | First resistive element |
| 52 | Second resistive element |
| 53 | Power source |
| 6 | Primary core wire |

BEST MODE(S) FOR CARRYING OUT THE INVENTION

Referring to the drawings, examples of a gas sensor heater coil, a gas sensor detecting element, a catalytic combustion gas sensor, and a manufacturing method of the catalytic combustion gas sensor according to the present invention will be described in detail below. The present invention is not limited to the examples.

FIG. 1 is a front view showing a structure of a heater coil according to an embodiment of the present invention. As shown in FIG. 1, in the embodiment, a bead portion 24 of a heater coil 22 is constituted of, for example, a double coil. Lead portions 25 of the heater coil 22 are constituted of, for example, single coils. To manufacture this heater coil 22, a single coil is manufactured by winding a resistive wire (raw wire) made of an ordinary non-coiled wire material, on a primary core wire. Using this single coil as a new plain wire, a portion for making the bead portion 24 is formed into a double coil by winding a portion of this plain wire on a secondary core wire. The secondary core wire may be a wire having the same diameter as that of the primary core wire or a different diameter from that of the primary core wire.

The lead portions 25 may be constituted of a coil wound into more than double fold and the bead portion 24 may be constituted of a coil wound into more than triple fold. For example, when the lead portions 25 and the bead portion 24 are respectively a double coil and a triple coil, a single coil is formed by winding a raw wire on a primary core wire, a double coil is formed by winding this single coil as a plain wire (primary plain wire) on a secondary core wire, a portion to be the bead portion 24 may be formed into a triple coil by winding a section of this double coil as a new plain wire (secondary plain wire) on a thirdly core wire. When the number of folds of the winding of the multi-wound portions of the coils of the lead portions 25 and the bead portion 24 are to be increased further, the number of times of repetition of the wire winding process to wind a plain wire on a core wire may be increased.

Figure 2:
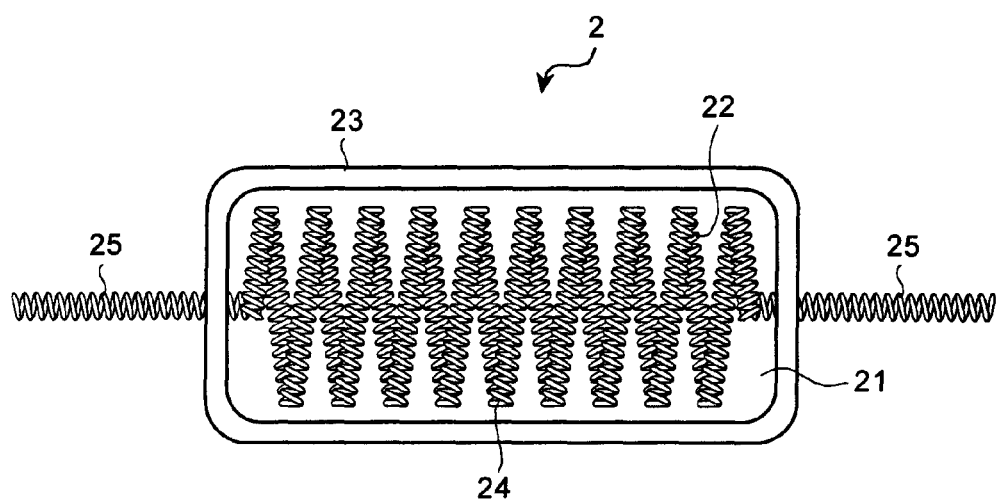
FIG. 2 is a cross-sectional view showing a structure of a detecting element according to the embodiment of the present invention.

FIG. 2 is a cross-sectional view showing a structure of a detecting element according to the embodiment of the present invention. As shown in FIG. 2, a detecting element 2 has a constitution that the bead portion 24 of the heater coil 22 is covered by a heat conductive layer 21 constituted of a sintered body, and a catalyst layer 23 is adhered on the surface of the heat conductive layer 21. The heat conductive layer 21 is constituted of, for example, alumina (aluminum oxide). The catalyst layer 23 is constituted of a combustion catalyst consisting of a metal oxide corresponding to the combustible gas to be detected. The catalyst layer 23 is heated to a temperature corresponding to the combustible gas to be detected by being applied with a voltage across both sides of the heater coil 22.

As a gas to be detected, for example, methane gas, hydrogen has, LP gas (Liquefied Petroleum gas), propane gas, butane gas, ethylene gas, carbon monoxide gas, or organic component gases such as ethanol, acetone, etc., can be listed.

When the gas to be detected is, for example, methane gas, the catalyst layer 23 is heated to approximately 450° C.

Figure 3:
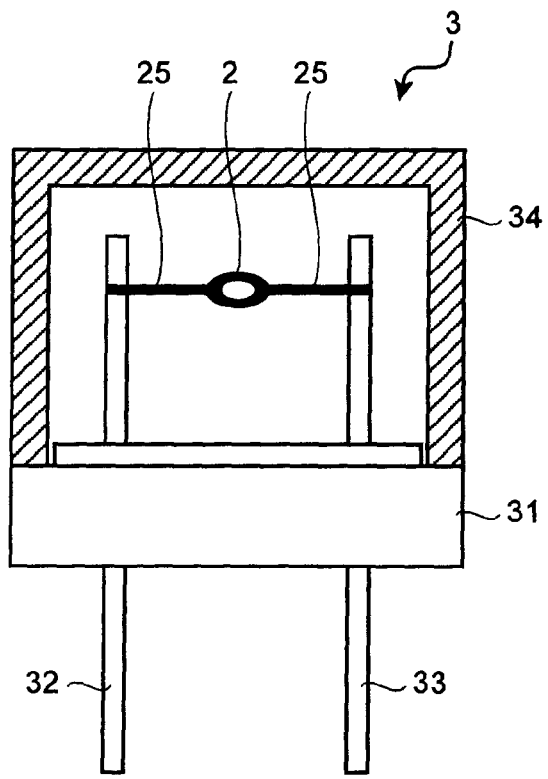
FIG. 3 is a partial cross-sectional view showing a structure of a sensor main body of a catalytic combustion gas sensor according to the embodiment of the present invention.

FIG. 3 is a partial cross-sectional view showing a structure of a sensor main body of the catalytic combustion gas sensor according to the embodiment of the present invention. As shown in FIG. 3, a sensor main body 3 has a constitution that the body 31 has electrode pins 32, 33 for external connection that penetrate a mount base 31 having a board-like shape and made of ceramic or resin and the lead portions 25 on both ends of the detecting element 2 is fixed to the electrode pins 32, 33. Though not shown in FIG. 3, a compensating element having a heater coil that has the same structure as that of the heater coil 22 of the detecting element 2 is provided beside the detecting element 2. This compensating element and the detecting element 2 are surrounded by the mount base 31 and an explosion-proof structure 34 formed with wire nets or a metal or ceramic sintered body having gas permeability.

Figure 4:
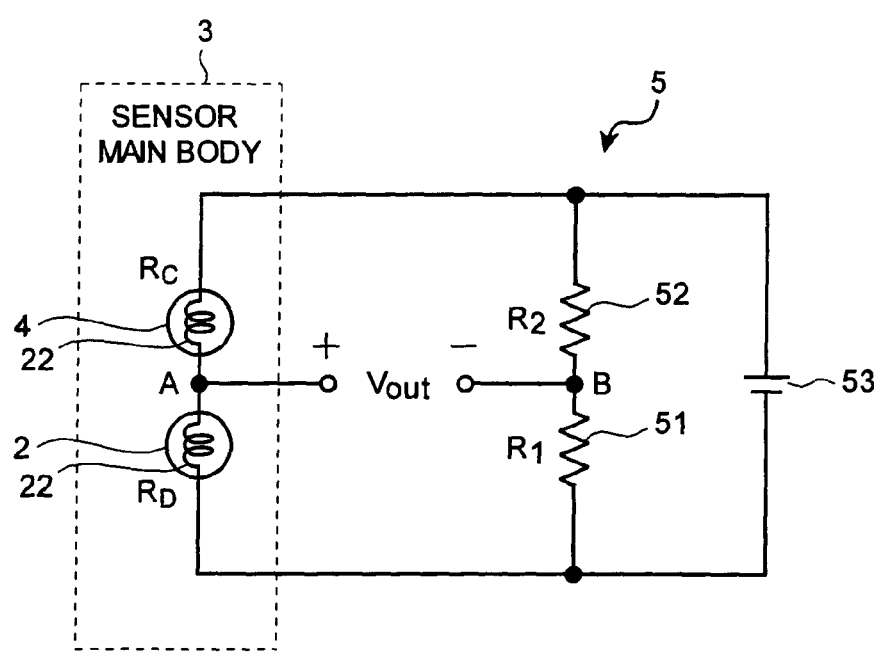
FIG. 4 is a circuit diagram showing a configuration of a control circuit of the catalytic combustion gas sensor according to the embodiment of the present invention.

FIG. 4 is a circuit diagram showing a configuration of a control circuit of the catalytic combustion gas sensor according to the embodiment of the present invention. As shown in FIG. 4, the control circuit of a catalytic combustion gas sensor 5 includes the detecting element 2, a compensating element 4 connected in series with the detecting element 2, a first resistive element 51, a second resistive element 52 connected in series with the first resistive element 51, and a power source (power source circuit) 53. The detecting element 2, the compensating element 4, the first and the second resistive element 51, 52 form a Wheatstone bridge circuit.

The power source 53 applies a DC voltage across both ends respectively of a connected-in-series body of the detecting element 2 and the compensating element 4, and a connected-in-series body of the first resistive element 51 and the second resistive element 52. From this Wheatstone bridge circuit, a voltage across a connecting node (indicated by A in FIG. 4) between, the detecting element 2 and the compensating element 4, and a connecting node (indicated by B in FIG. 4) between the first resistive element 51 and the second resistive element 52 is output. Describing energized-state resistance values of the detecting element 2, the compensating element 4, the first resistive element 51, and the second resistive element 52 respectively as $R_D$, $R_C$, $R_1$, and $R_2$, an output voltage $V_{out}$ of the Wheatstone bridge circuit is zero volt when $[R_C \times R_1 = R_D \times R_2]$.

When a nominal voltage is applied by the power source 53 across each heater coil 22 of the detecting element 2 and the compensating element 4, each heater coil 22 generates heat and the detecting element 2 and the compensating element 4 are at the operating temperature that corresponds to a gas to be detected. The output voltage $V_{out}$ corresponding to the energized-state resistance values obtained at an equilibrium temperature to the environment is obtained from the gas sensor 5. When a gas to be detected has been detected, only the energized-state resistance voltage $R_D$ of the detecting element 2 is increased by catalytic combustion of the gas to be detected. Therefore, the output voltage $V_{out}$ is increased to the + (plus) side by the amount corresponding to the gas sensitivity.

The catalyst operating temperature to cause the gas to be detected to burn by catalyst at high efficiency is selected based on a kind of the gas. When a heater coil having a larger resistance value is employed, a higher power source voltage is necessary to obtain a desired catalyst operating temperature. Because the power source voltage and the output voltage $V_{out}$ of the bridge circuit are in a proportional relation due to the nature of the bridge circuit, the gas sensitivity obtained when a heater coil having a higher resistance value is employed is a higher value. That is, the heater coil 22 having the structure described above has a higher resistance value than that of a conventional heater coil as described later, and therefore, high gas sensitivity can be obtained by employing this heater coil 22.

Specific characteristics of the heater coil 22 will be described. As a raw wire to constitute the heater coil 22, for example, platinum or platinum alloy wire, alloy wire based on platinum or platinum alloy such as platinum or platinum alloy-rhodium alloy, or iron-palladium alloy wire can be used. The wire diameter of the raw wire is equal to or larger than 1 μm and equal to or smaller than 100 μm. The reason thereof is that manufacture of the double coil constituting the bead portion 24 is difficult because the wire is too thin when the wire diameter of the raw wire is smaller than 1 μm while the sintered body of the detecting element 2 is too large when the wire diameter of the raw wire exceeds 100 μm.

The wire diameter of the raw wire may be preferably equal to or larger than 10 μm and equal to or smaller than 50 μm. The reason thereof is that the power source 53 having an appropriate voltage-current value can be used, and thus, the catalyst layer 23 can be maintained at an appropriate operating temperature during operation of the catalytic combustion gas sensor 5. For example, when the wire diameter of the raw wire is 50 μm, a power source having the voltage-current value of 0.75 V-400 mA can be used. When the wire diameter of the raw wire is 10 μm, a power source having the voltage-current value of 12 V-25 mA can be used.

The wire diameter of the raw wire may be preferably equal to or larger than 20 μm and equal to or smaller than 30 μm. The reasons thereof are as follows. First, the lead portions 25 of the heater coil 22 can sufficiently support the detecting element 2 because the weight of the combusting portion of the detecting element 2 is approximately 1 mg. Second, the anti-shock strength of the catalytic combustion gas sensor 5 is improved. Third, the ability of the heater coil 22 to receive heat is improved and the resistance variation of the heater coil 22 during combustion is generated more efficiently, and therefore, the response speed of the catalytic combustion gas sensor 5 is improved because the bead portion 24 of the heater coil 22 can be more densely buried in the combusting portion of the detecting element 2. Fourth, the resistance of the heater coil 22 is increased by thinning the wire, thereby increasing the power source voltage as described above, and therefore, the gas sensitivity of the catalytic combustion gas sensor 5 is improved. Fifth, the yield obtained in the manufacture of the heater coil 22 is degraded when the wire diameter of the raw wire is smaller than 20 μm.

Table 1 collectively shows the relation among the wire diameter of the raw wire of the heater coil 22, the weight of the combusting portion of the detecting element 2, the gas sensitivity of the catalytic combustion gas sensor 5, and the response time of the catalytic combustion gas sensor 5. In Table 1, all of the relative weight (a.u.), the relative gas sensitivity (a.u.), and the relative response time (a.u.) for each wire diameter range are relative values to the weight (1 mg), the gas sensitivity (40 mV), and the response time (five seconds) of the combusting portion obtained when a heater coil using a platinum wire having the diameter of 30 μm as the raw wire thereof is employed. The bead portion 24 and the lead portions 25 are respectively a double coil and single coils. The gas sensitivity is gas sensitivity to 4,000 ppm of hydrogen gas. The response time is the necessary time for reaching to 90% or more of the output stable value for 4,000 ppm of hydrogen gas.

TABLE 1

| Wire Diameter range (μm) | 1 to 20 | 20 to 30 | 30 to 50 | 50 to 100 | Example: 30 μm |
|---|---|---|---|---|---|
| Relative weight (a.u.) | 0.01 to 0.5 | 0.5 to 1.0 | 1.0 to 1.5 | 1.5 to 2.5 | 1 μg |
| Relative gas sensitivity (a.u.) | 10 to 2.5 | 2.5 to 1.0 | 1.0 to 0.4 | 0.4 to 0.1 | 40 mV |
| Relative response time (a.u.) | 0.5 to 1 | 0.5 to 1 | 1 to 2 | 2 to 3 | 5 sec |

The winding diameter of a single-wound coil is equal to or larger than 0.5 times and equal to or smaller than 20 times as large as the diameter of the core metal (primary core wire) used for winding the raw wire in a coil. Similarly, the winding diameter of a double coil is equal to or larger than 0.5 times and equal to or smaller than 20 times as large as the diameter of the core metal used for winding the single coil (plain wire) further in a coil. The same is applied to the case of a triple or more-fold coil. The reason thereof is that the lead portions 25 of the heater coil 22 can sufficiently support the detecting element 2 because the combusting portion of the detecting element 2 is not heavy. When the winding diameter exceeds the length that is 20 times as large as the core metal, the amount of the heat conductive layer 21 filled in an internal space of the coil of the bead portion 24 is increased and the combusting portion becomes heavy, and therefore, the supporting performance of the lead portions 25 against the detecting element 2 is degraded and the shock-resisting performance of the catalytic combustion gas sensor 5 may become lower than the practically-permitted range.

The winding diameter of a single coil is preferably equal to or larger than one time, and equal to or smaller than 10 times as large as the diameter of the core metal used for winding the raw wire in a coil. Similarly, the winding diameter of a double coil is equal to or larger than one time, and equal to or smaller than 10 times as large as the diameter of the core metal used for winding the single coil (plain wire) further in a coil. The same is applied to the case of a triple or more fold coil. The reason thereof is that the heater coil 22 can be obtained at a high yield and the supporting performance of the lead portions 25 against the detecting element 2 can be stably obtained because the shape stability of the coil after the winding process is excellent. Though the winding diameter is equal to or smaller than 20 times as large as the diameter of the core metal, if the winding diameter exceeds 10 times as large as the diameter of the core metal, the shape stability of the coil after the winding process is degraded to some extent.

The number of turns of the double coil that is the final helicoid is equal to or more than 1 and equal to or less than 30. The same is applied to the case where the final helicoid is a triple or more fold coil. The reason thereof is that the lead portions 25 of the heater coil 22 can sufficiently support the detecting element 2 because the combusting portion of the detecting element 2 is not heavy. When the number of turns exceeds 30, the combusting portion becomes heavy, and therefore, the lead portions 25 of the heater coil 22 can not stably support the detecting element 2. Especially, the appropriate number of turns of the double coil is 4 to 10.

In the double coil that is the final helicoid, the length of a gap between a wound portion 26 and a wound portion 27 that is next to the wound portion 26, that is, an inter-plain-wire gap distance of the single coil that is a plain wire, is equal to or larger than 0.5 times and equal to or smaller than 10 times as large as the diameter of the plain wire. The same is applied to the case where the final helicoid is a triple or more fold coil. The reasons are as follows. First, a sufficiently quick response property can be obtained. Second, the adjacent wound portions 26, 27 can be prevented from shorting with each other when the detecting element 2 is manufactured. Third, the catalyst layer 23 can be formed by filling the heat conductive layer 21 in the internal space of the coil of the bead portion 24. The length of the gap between the wound portion 26 and the wound portion 27 that is next to the wound portion 26 (the inter-plain-wire gap distance) is a distance obtained by subtracting halves of the thickness of respectively the wound portion 26 and the wound portion 27 from the distance between the wires that is generally referred to as "pitch" for a helicoid.

Table 2 shows the relation between the inter-plain-wire gap distance of the heater coil 22 and the response time of the catalytic combustion gas sensor 5. In Table 2, the inter-plain-wire gap distance is expressed by a magnification to the diameter of the plain wire. The relative response time (a.u.) for each range of the inter-plain-wire gap distance is a relative value to a response time obtained when a heater coil having an inter-plain-wire gap distance that is equal to the diameter of the plain wire is employed. The bead portion 24 and the lead portions 25 are respectively double coil and single coils.

TABLE 2

| Inter-plain-wire gap distance (*) | 0.5 to 1 | 1 to 2.5 | 1.25 to 2 | 2 to 10 |
|---|---|---|---|---|
| Relative response time (a.u.) | 0.5 to 1 | 1 to 1.5 | 1.6 to 2 | 2 to 10 |

(*) Magnification of the plain wire to the diameter

Figure 18:
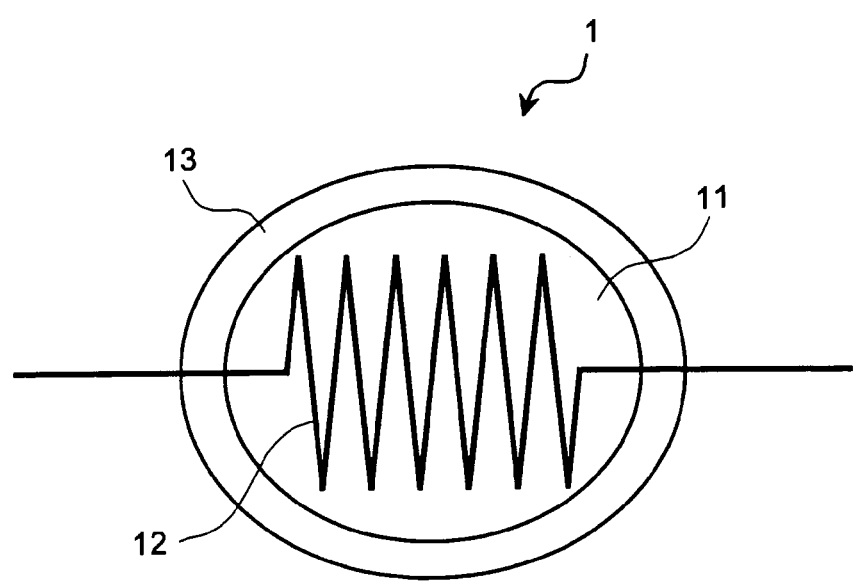
FIG. 18 is a cross-sectional view showing a structure of a conventional detecting element.
Figure 19:
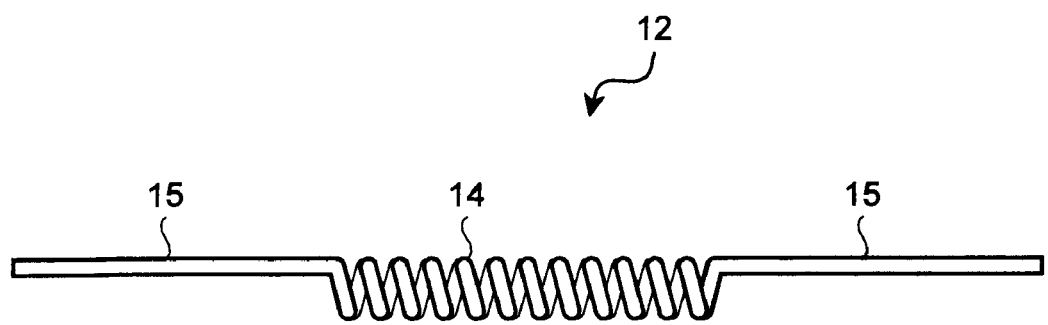
FIG. 19 is a front view showing a structure of a conventional heater coil.

The result of comparison of performance as a gas sensor between the catalytic combustion gas sensor 5 (as an example) employing the heater coil 22 having the constitution shown in FIG. 1 and the catalytic combustion gas sensor (as a conventional example) employing the heater coil 12 having the constitution shown in FIG. 19 will be described. In this comparison of performance, catalysts respectively having a same composition, etc., were used in the example and the conventional example. The operating temperature of the combustion catalyst was made equal. For five samples for the example, the average value of the effective lengths (see FIG. 2) of the bead portions 24 respectively buried in the combusting portions of the detecting elements 2 was 75 mm. For five samples for the conventional example, the average value of the effective lengths (see FIG. 18) of the bead portions 14 respectively buried in the combusting portions of the detecting elements 1 was 15 mm. Other conditions were all same.

Table 3 shows the result of comparison of the gas sensitivity. Using a value obtained by subtracting the output voltage value in the atmosphere from the output voltage value in a gas as "gas sensitivity", two types of comparison including comparison of the sensitivity to 4,000 ppm of hydrogen gas and comparison of sensitivity to 4,000 ppm of methane gas were performed. The gas sensitivity of the samples for the example was approximately three times as high as the gas sensitivity of the samples for the conventional example.

TABLE 3

| | $H_2$ (4,000 ppm) | | $CH_4$ (4,000 ppm) | (Unit: mV) |
|---|---|---|---|---|
| No. | Example | Conventional example | Example | Conventional example |
| 1 | 90 | 31 | 58 | 19 |
| 2 | 89 | 33 | 51 | 20 |
| 3 | 85 | 32 | 58 | 20 |
| 4 | 97 | 31 | 56 | 18 |
| 5 | 102 | 29 | 51 | 16 |

Table 4 shows the result of the comparison of the response speed. The time necessary for reaching 90% or more of the output stable value for 1,800 ppm of hydrogen gas is listed in Table 4 as the response time. The response time of the samples for the example was approximately half of the response time of the samples of the conventional example. That is, the response speed of the samples of the example was approximately two times as high as the response speed of the samples of the conventional example.

TABLE 4

| No. | Example | Conventional Example | (Unit: second) |
|---|---|---|---|
| 1 | 2 | 5 | |
| 2 | 3 | 6 | |
| 3 | 2 | 5 | |
| 4 | 2 | 5 | |
| 5 | 3 | 6 | |

Table 5 shows the result of the comparison of the zero point variation (hydrogen-concentration-converted value) generated after an impact applied by being dropped down. Each of the catalytic combustion gas sensors of the example and the conventional example was dropped down to free-fall from a height of 1 m onto a cedar board of 30 mm thick. As the hydrogen-concentration-converted values, the variation of the zero point after the impact applied by the falling was equal to or smaller than 2,000 ppm for the example while the variation exceeded 2,000 ppm for the conventional example.

TABLE 5

| Example | Equal to or less than 2,000 ppm |
|---|---|
| Conventional example | More than 2,000 ppm |

Figure 5:
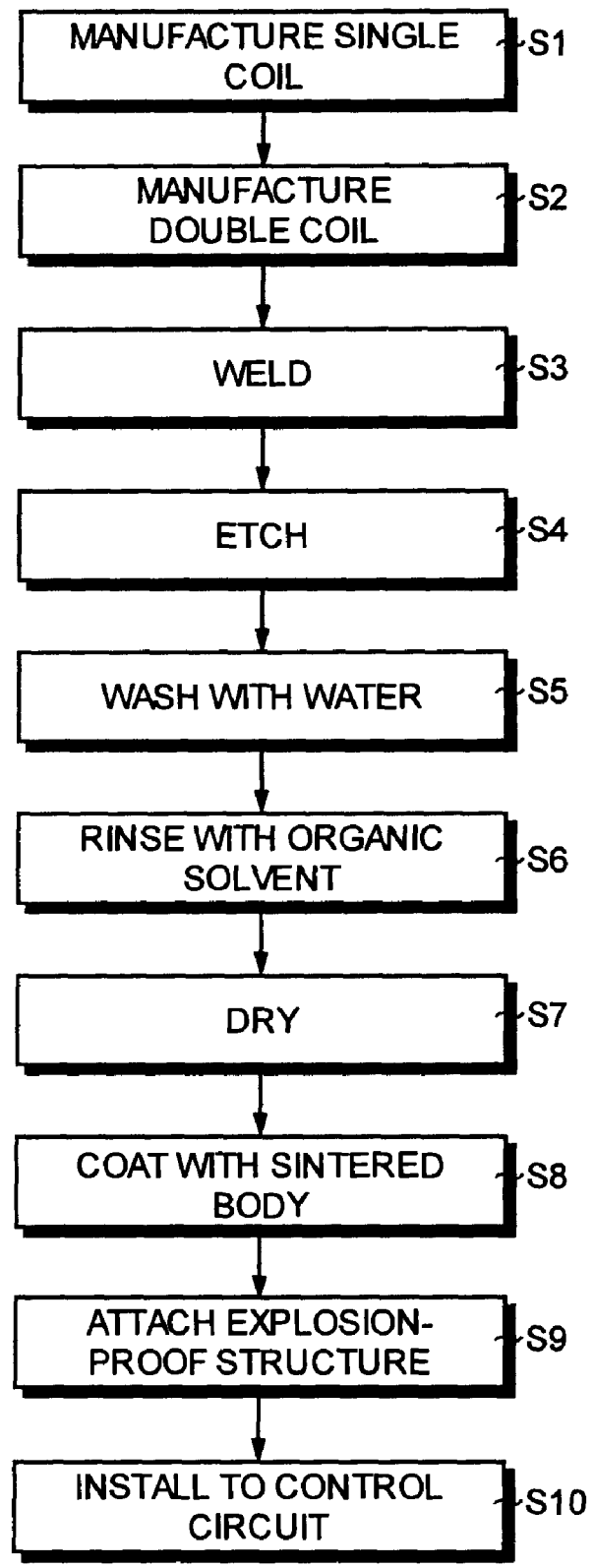
FIG. 5 is a flowchart showing a manufacturing method of the catalytic combustion gas sensor according to the embodiment of the present invention.
Figure 6:
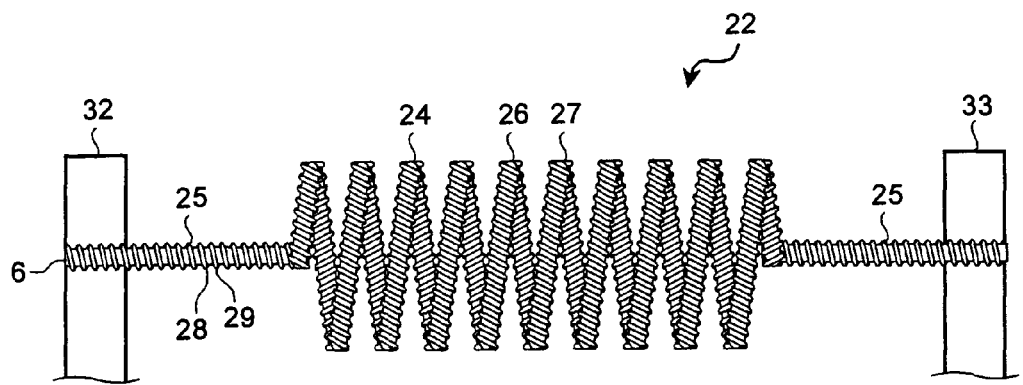
FIG. 6 is a partial enlarged view showing an in-process state during manufacture of the catalytic combustion gas sensor according to the embodiment of the present invention.
Figure 7:
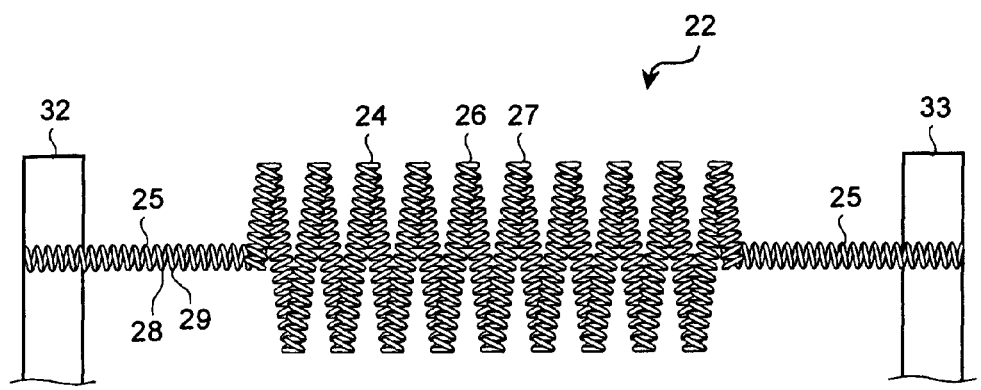
FIG. 7 is a partial enlarged view showing an in-process state during manufacture of the catalytic combustion gas sensor according to the embodiment of the present invention.

A manufacturing method of the catalytic combustion gas sensor 5 will be described. FIG. 5 is a flowchart showing the manufacturing method. FIGS. 6 and 7 are partial enlarged views showing in-process states during the manufacture. An ordinary non-coiled resistive wire is prepared and a single coil is formed by winding this wire on a primary core wire (step S1).

The primary core wire may be any wire material that is made of more basic metal than that of the resistive wire used. This is because, in a wet etching process performed later, it is necessary to melt the primary core wire leaving the resistive wire as it is. The primary core wire is made of, for example, nickel, aluminum, copper, stainless alloy, etc. The appropriate diameter of the primary core wire is 20 to 60 μm. In the single coil, the appropriate length of a gap between a wound portion 28 and a wound portion 29 (see FIG. 7) that is next to the wound portion 28, that is, the appropriate inter-plain-wire gap distance of the plain wire is equal to or larger than 0.5 times and equal to or smaller than 10 times as large as the diameter of the plain wire.

A double coil is formed by winding a portion of the single coil, that is, the portion to form the bead portion 24 on a secondary core wire as the heater coil 22 (step S2). Though the material of the secondary core wire is not limited especially, the material is, for example, hard metal, hardened steel, etc. The appropriate diameter of the secondary core wire is 100 μm to 300 μm.

The most preferable combination of the plain wire (the resistive wire), the primary core wire, the single coil, the secondary core wire, and the double coil is as follows. That is, the plain wire is a platinum or platinum alloy wire having the diameter of 20 μm and the primary core wire is a nickel wire having the diameter of 40 μm. For this combination, the inter-plain-wire gap distance of the plain wire is preferably 20 μm. As the most preferable combination, the diameter of the primary plain wire constituted of the single coil is 80 μm (20 μm (the diameter of the plain wire)+40 μm (the diameter of the primary core wire)+20 μm (the diameter of the plain wire)). For the double coil employing this combination, the inter-plain-wire gap distance considered based on the single coil as the plain wire is preferably 80 μm.

After the secondary core wire has been pulled out, the lead portions 25 on both ends of the heater coil 22 is welded to the electrode pins 32, 33 extruded from the mount base 31 in a resistance welding method, a laser welding method, or a thermo-compression bonding method (step S3). At this point, as shown in FIG. 6, the primary core wire 6 still remains.

The electrode pins 32, 33 are made of, for example, nickel or nickel-copper alloy (monel metal). Otherwise, the corrosion resistance of the electrode pins 32, 33 can be facilitated by constituting the pins 32, 33 with nickel-chromium-molybdenum alloy such as Inconel, Hastelloy (commercial names), etc., stainless alloy such as SUS316L, etc., titanium or titanium alloy, or a combination thereof. The most preferable material as the material of the electrode pins 32, 33 is Hastelloy (product name). Though not limited especially, the diameter of the electrode pins 32, 33 is, for example, approximately 600 μm.

Though any method can be employed as the method for welding, the resistance welding method is preferable. The reason thereof is that, when the resistance welding method is employed, the rise of the voltage of the welding apparatus is extremely quick and the energizing duration can be controlled stably on the millisecond-order, and therefore, as in the embodiment, the method is suitable for welding different materials with each other, for welding very thin metal lines, etc.

When the resistance welding method is implemented, a known transistor resistance welding apparatus can be used. Though the conditions for welding in this case are not especially limited, the appropriate conditions are, for example, the voltage is 2.0 V to 3.0 V, the energizing time is three milliseconds, and the head load is 0.5 kgf to 5 kgf. In the case of the most preferable combination described above of the primary core wire, the single coil, the secondary core wire, and the double coil, the voltage value is preferably 2.3 V.

The primary core wire 6 is melted and eliminated by soaking the electrode pins 32, 33 with the heater coil 22 welded thereto in an etching liquid (step S4). At this step, by performing the etching after covering the welded portion between the heater coil 22 and the electrode pins 32, 33, the primary core wire 6 may be left only in the welded portion.

The etching liquid is, for example, a water mixture solution of nitric acid (30%), sulfuric acid (3%), and hydrogen peroxide (2%), or a ferric chloride solution (40% water solution).

When the water mixture solution of nitric acid, sulfuric acid, and hydrogen peroxide is used, the appropriate bath temperature is the room temperature (for example, 25° C.) and the appropriate soaking time is 60 minutes. When the ferric chloride solution is used, the appropriate bath temperature is 40° C. and the appropriate soaking time is three minutes.

When the etching has been completed, the heater coil 22 with the electrode pins 32, 33 welded thereto is lifted up from the etching liquid and is washed with water (step S5), and is rinsed with an organic solvent such as isopropylalcohol (IPA), etc. (step S6), and is dried (step S7). FIG. 7 shows the state where the primary core wire has been eliminated by the etching.

Slurry including a heat conducting material, a combustion catalyst, etc., is applied on the bead portion 24 of the heater coil 22, and the slurry and the bead portion are heated and burned (step S8). The sensor main body 3 is fabricated by attaching the explosion-proof structure 34, etc., (step S9). Finally, the sensor main body 3 is installed to the control circuit (step S10), and the catalytic combustion gas sensor 5 is completed by performing the zero-point adjustment, etc., of the sensor.

The specific numerical values, materials, etc., of the most preferable combination of the plain wire (resistive wire), the primary core wire, the single coil, the secondary core wire, and the double coil; the conditions of the welding; the conditions of the etching, etc., described above are those that have turned out in the experiments conducted by the inventors.

Characteristic points that have appeared in the bonding interface between the heater coil 22 and the electrode pins 32, 33 due to the manufacture following the manufacturing method described above will be described. As an example, a non-coil platinum or platinum alloy wire having the diameter of 20 μm was used as the plain wire and the single coil was formed by winding this plain wire on the primary core wire 6 constituted of a nickel wire having the diameter of 40 μm taking an inter-plain-wire gap distance of 20 μm. The double coil was formed by winding this single coil on the secondary core wire constituted of a hard metal wire having the diameter of 150 μm for six turns taking an inter-plain-wire gap distance of 80 μm. The lengths of the lead portions 25 on both ends of the bead portion 24 were respectively 1 mm.

The electrode pins 32, 33 were formed with Hastelloy having the diameter of 600 μm and the resistance welding method was employed. The conditions of welding were same as those described above except that the head load was 1.5 kgf and the voltage value was 2.3 V. The etching process was performed for 60 minutes using the water mixture solution of nitric acid, sulfuric acid, and hydrogen peroxide at a bath temperature of the room temperature.

Figure 8:
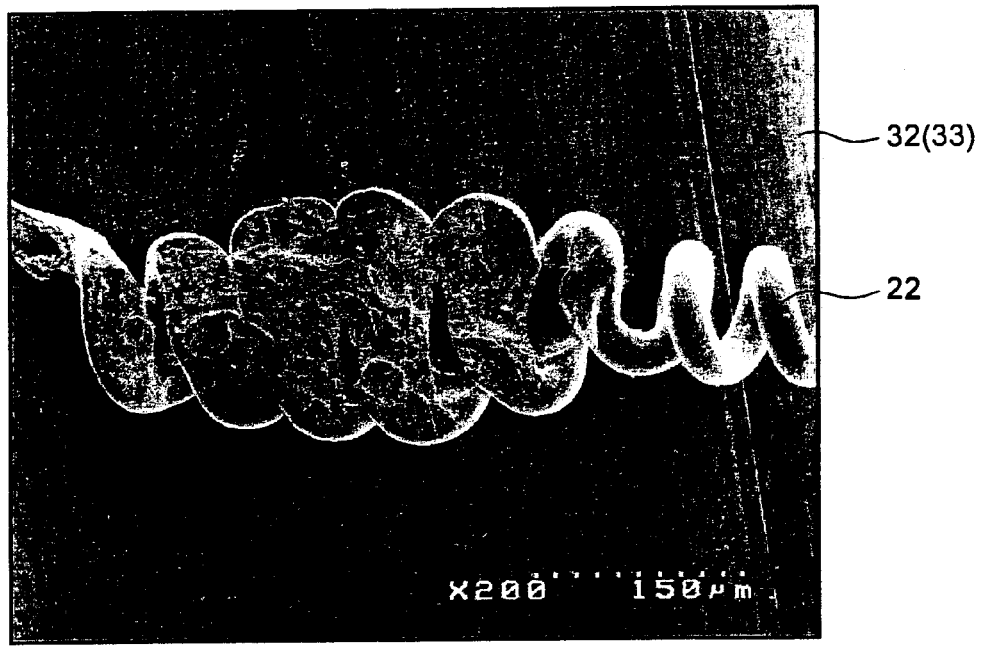
FIG. 8 is an explanatory view showing a SEM image showing a surface appearance of a welded portion of an example.
Figure 9:
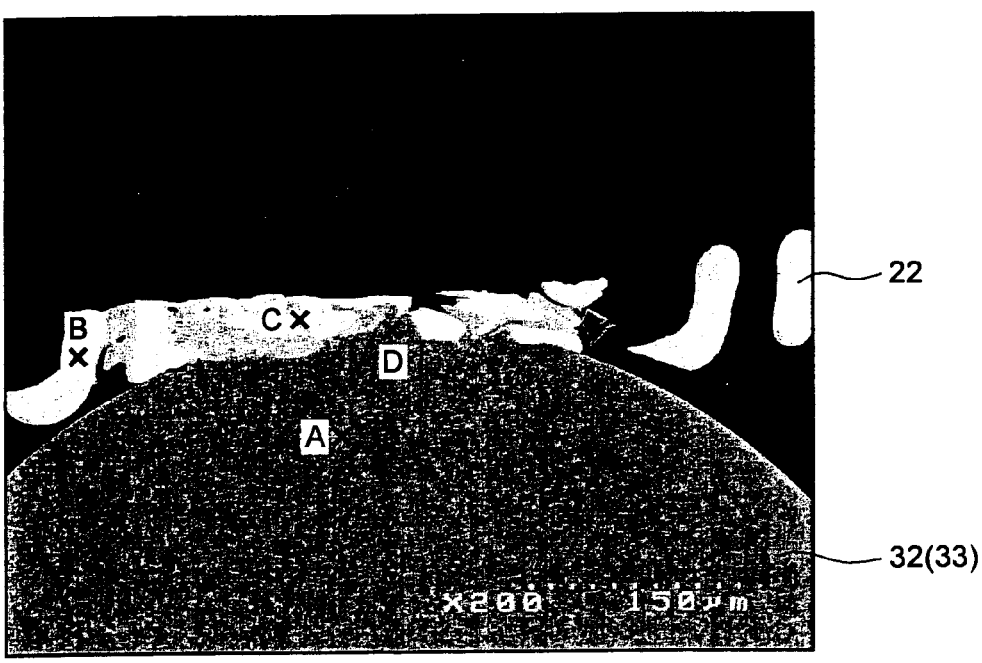
FIG. 9 is an explanatory view showing a SEM image showing a cross-section appearance of a welded portion of an example.
Figure 15:
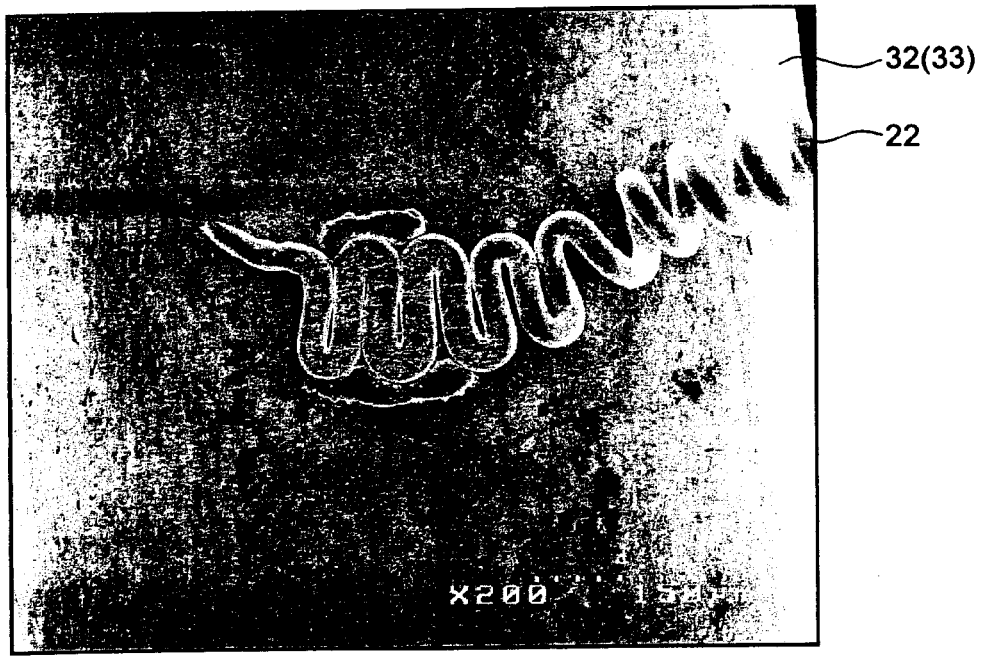
FIG. 15 is an explanatory view showing a SEM image of a surface of a welded portion of a comparative example.
Figure 16:
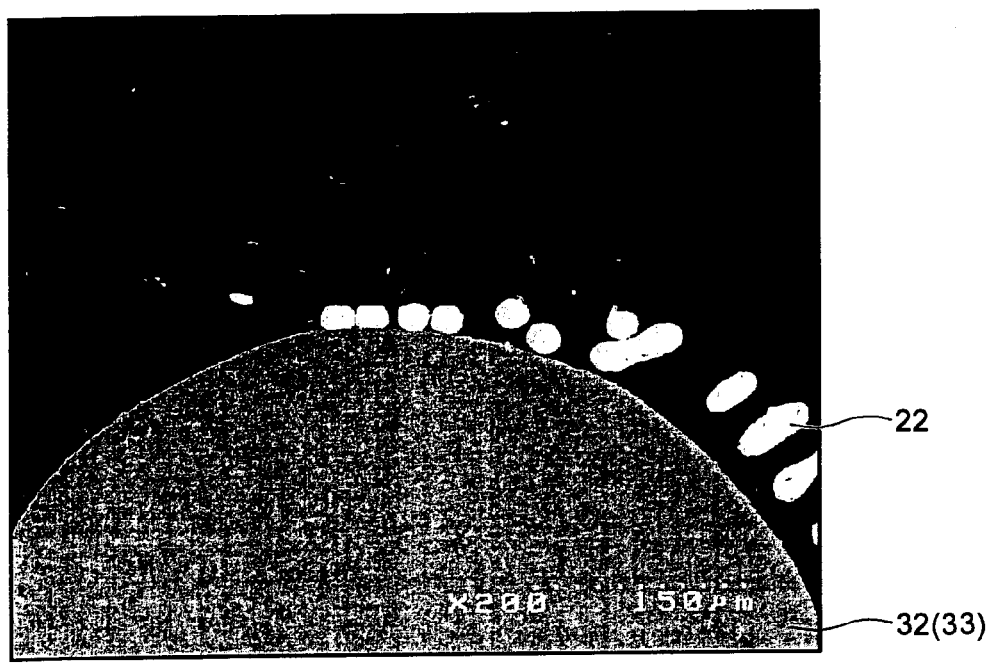
FIG. 16 is an explanatory view showing a SEM image of a cross-section of the welded portion of the comparative example.

The case where the heater coil 22 and the electrode pins 32, 33 are welded with each other with the primary core wire 6 remaining as it is taken as an example, and the case where the heater coil 22 and the electrode pins 32, 33 are welded with each other after the primary core wire 6 has been eliminated is taken as a comparable example. FIGS. 8 and 9 are photos respectively observing, with a scanning electron microscope, the surface and a cross-section of the welded portion of the example. FIGS. 15 and 16 are photos respectively observing, with a scanning electron microscope, the surface and a cross-section of the welded portion of the comparative example.

Comparing FIG. 8 with FIG. 15, it can be seen that each wound portion of the lead portions 25 of the heater coil 22 is bonded with the electrode pins 32, 33 more regularly and sufficiently crushed in the example than in the comparative example. Comparing FIG. 9 with FIG. 16, it can be seen that the bonded area is wider in the example than in the comparative example and the bonding interface is partially alloyed in the example. The alloying is also evident from the analysis result shown in FIGS. 10 to 13. FIG. 10, FIG. 11, FIG. 12, and FIG. 13 are charts respectively showing the analysis results by an X-ray micro-analyzer (XMA) at locations indicated by "A", "B", "C", and "D" of the cross-sectional photo of the example shown in FIG. 9.

Figure 10:
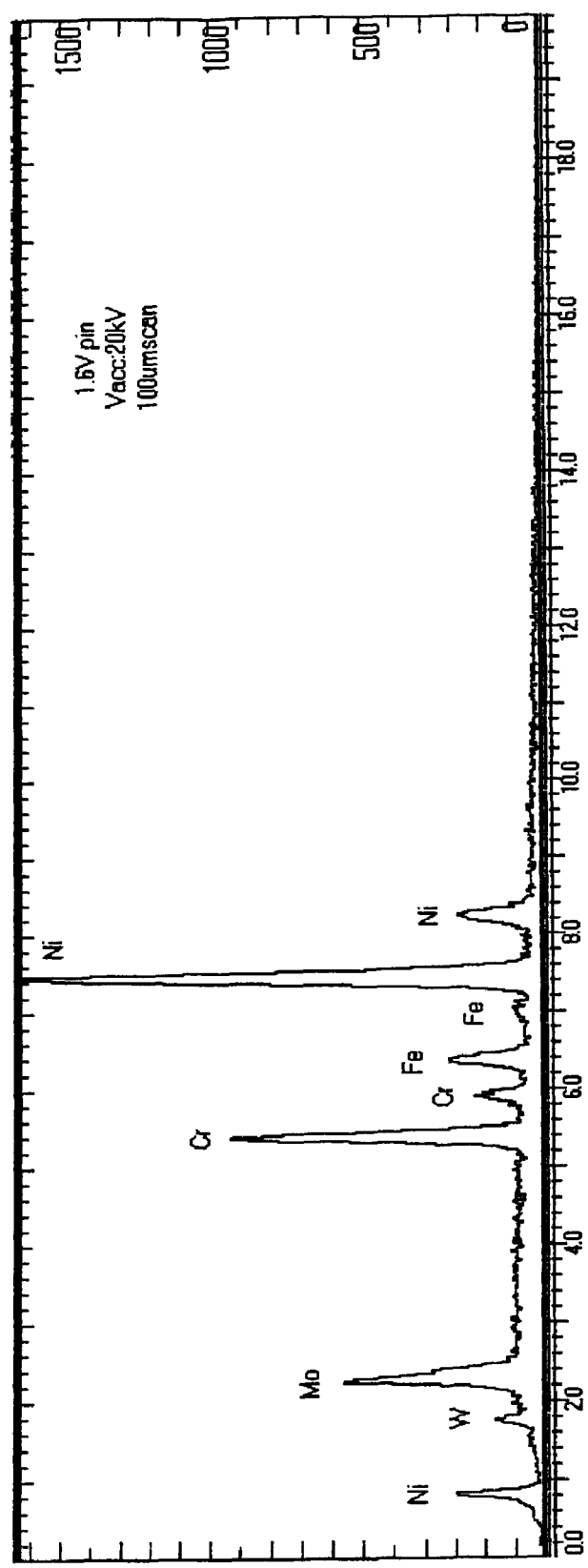
FIG. 10 is a chart showing an analysis result of XMA at a point A shown in FIG. 9.
Figure 11:
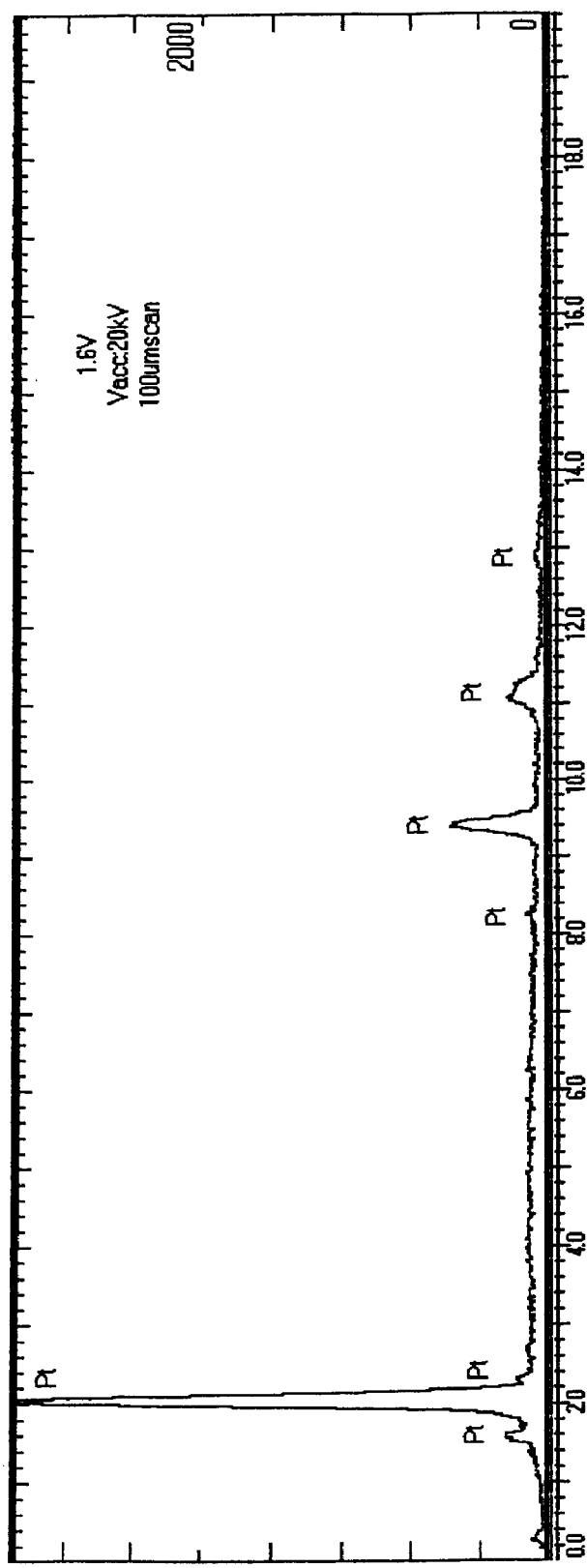
FIG. 11 is a chart showing an XMA spectrum at a point B shown in FIG. 9.
Figure 12:
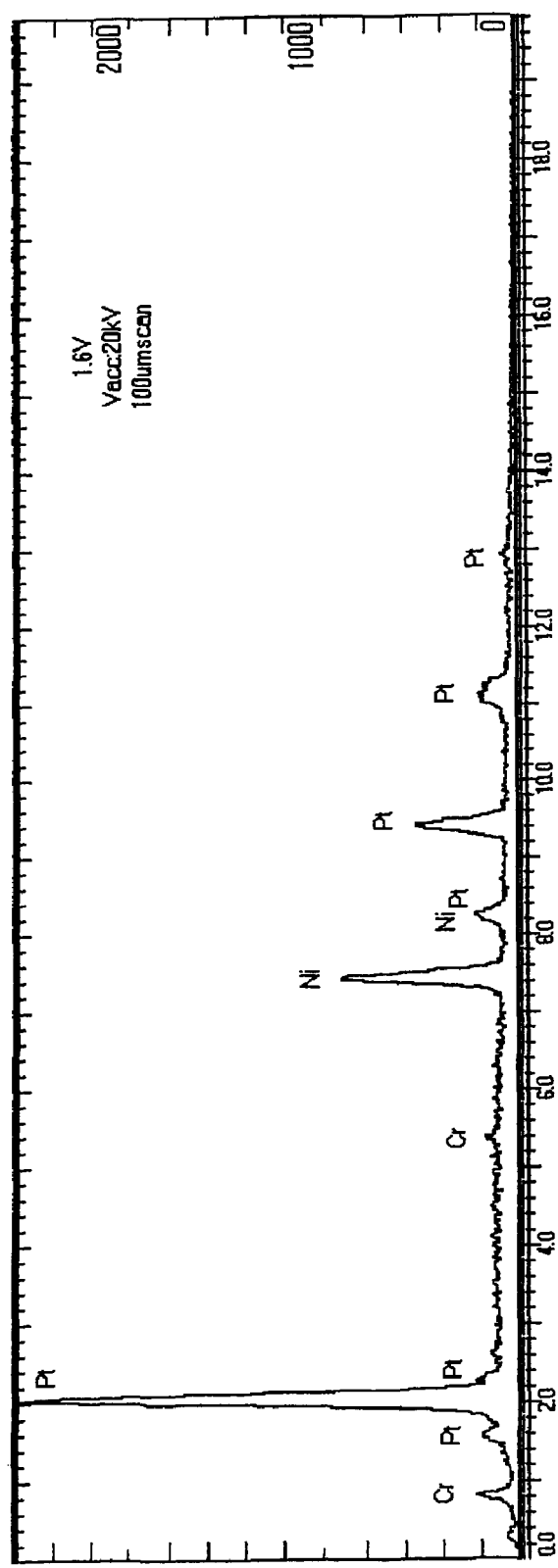
FIG. 12 is a chart showing the XMA spectrum at a point C shown in FIG. 9.
Figure 13:
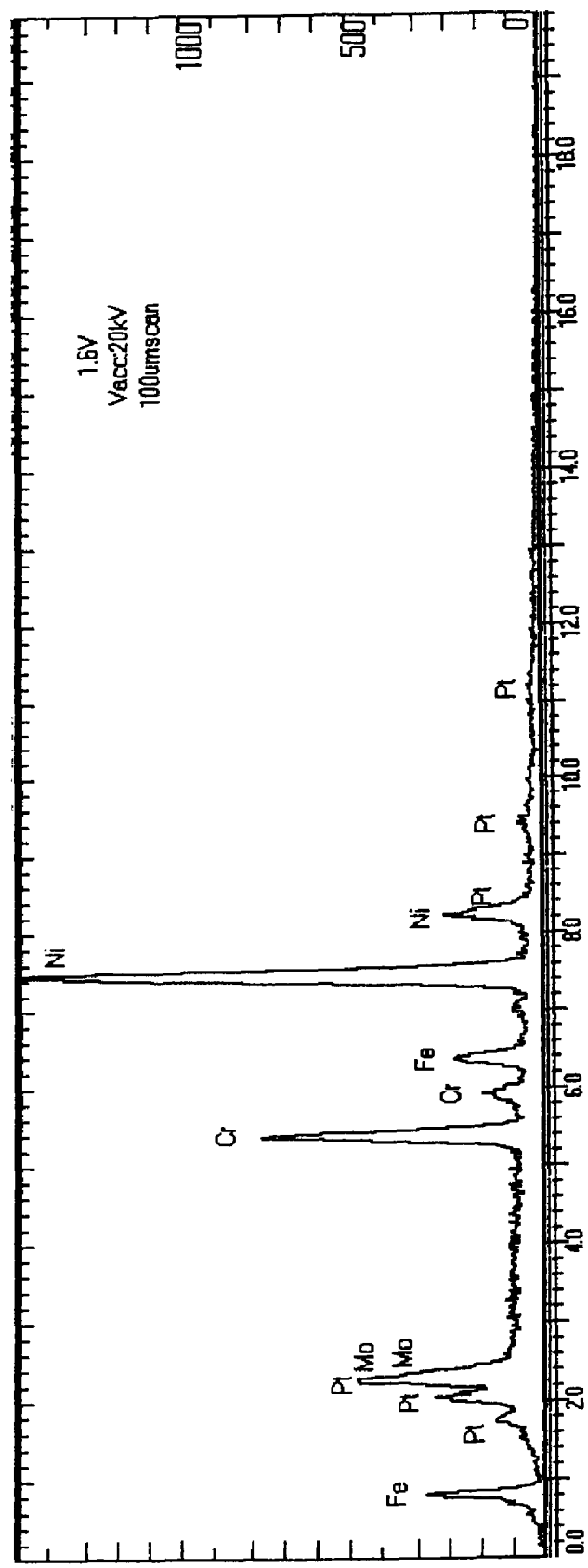
FIG. 13 is a chart showing an analysis result of XMA at a point A shown in FIG. 9.

At "A" that corresponds to the bulk of the electrode pins 32, 33, peaks of nickel, chromium, and molybdenum are observed and no peak of platinum or platinum alloy is observed (FIG. 10). At "B" that is a point having no bonding of the heater coil 22 with the electrode pins 32, 33, a peak of platinum or platinum alloy is observed and no peak of nickel, chromium, or molybdenum is observed (FIG. 11).

At "C" that is a portion close to the heater coil 22 in the bonding interface between the heater coil 22 and the electrode pins 32, 33 and "D" that is a portion close to the electrode pins 32, 33 in the bonding interface between the heater coil 22 and the electrode pins 32, 33, peaks of platinum or platinum alloy, nickel, and chromium are observed at both of the locations. This shows that, in the bonding interface of the heater coil 22 and the electrode pins 32, 33, the nickel of the primary core wire has acted as a brazing filler metal, and thus, the heater coil 22, the primary core wire 6, and the electrode pins 32, 33 have alloyed. Due to the presence of the primary core wire 6 made of nickel, the vicinity of the point "D" is a rich layer including a higher percentage of nickel than that of the bulk of the electrode pins 32, 33.

To confirm the improvement of the bonding strength obtained by alloying, 10 samples were prepared respectively for the example and the comparative example described above and measurement of anti-breakage strength was conducted using the samples. For the example, the samples for which steps S1 to S7 of FIG. 5 were performed, and for the comparative example, the samples for which steps S1 and S2 of FIG. 5 were performed, and after the primary core wire 6 had been eliminated by first performing step S4, the welding at step S3 was performed, and steps 5 to S7 were performed, were measured as to the strength at the moment of breakage of the heater coil 22 or the welded portion when the samples were pulled vertically at the heater coil 22 between the electrode pins 32, 33. To know the anti-breakage strength of a platinum or platinum alloy wire, the strength at the moment of breakage of the platinum or platinum alloy wire was measured when both ends of the platinum or platinum wire having the diameter of 20 μm and the length of 50 mm were pulled. Table 6 shows the measurement result.

TABLE 6

| Example (bonded with core wire) | Comparative example (bonded without core wire) | φ20 μm platinum wire tensile strength |
|---|---|---|
| 20.5 | 15.2 | 19.3 |
| 19.1 | 14.6 | 20.2 |
| 20.0 | 17.6 | 19.9 |
| 19.8 | 18.2 | 20.0 |
| 19.4 | 13.5 | 20.3 |
| 19.4 | 16.2 | 19.4 |
| 19.9 | 14.5 | 19.6 |
| 20.0 | 18.6 | 19.7 |
| 19.9 | 15.2 | 20.1 |
| 19.3 | 15.2 | 19.9 |

TABLE 6-continued

|  | Example (bonded with core wire) | Comparative example (bonded without core wire) | φ20 µm platinum wire tensile strength |
|---|---|---|---|
| Average value | 19.7 | 15.7 | 19.8 |
| Maximum value | 20.5 | 18.6 | 20.3 |
| Minimum value | 19.1 | 13.5 | 19.3 |

All of the samples for the example broke in the middle of the heater coils 22 thereof. The anti-breakage strength of each of the samples was approximately equal as the tensile strength of a platinum or platinum alloy wire having the diameter of 20 µm. In contrast, the anti-breakage strength of each of the 10 samples for the comparative example was lower than the tensile strength of a platinum or platinum alloy wire having the diameter of 20 µm, and the welded portion of the heater coil 22 and the electrode pins 32, 33 of each sample was broken. From this fact, it was confirmed that sufficiently high bonding strength that is equal to or larger than the tensile strength of a platinum or platinum alloy wire can be obtained when welding is performed with the primary core wire 6 remaining as it is.

Figure 14:
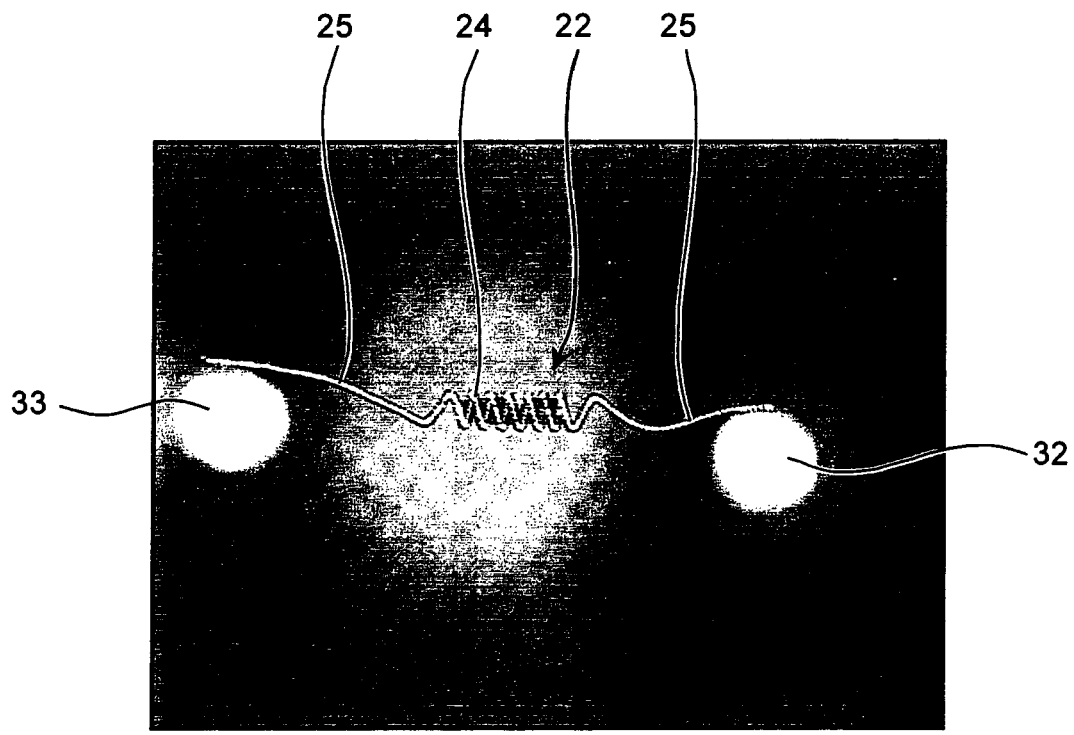
FIG. 14 is a photograph showing an entire shape of a heater coil of the example.
Figure 17:
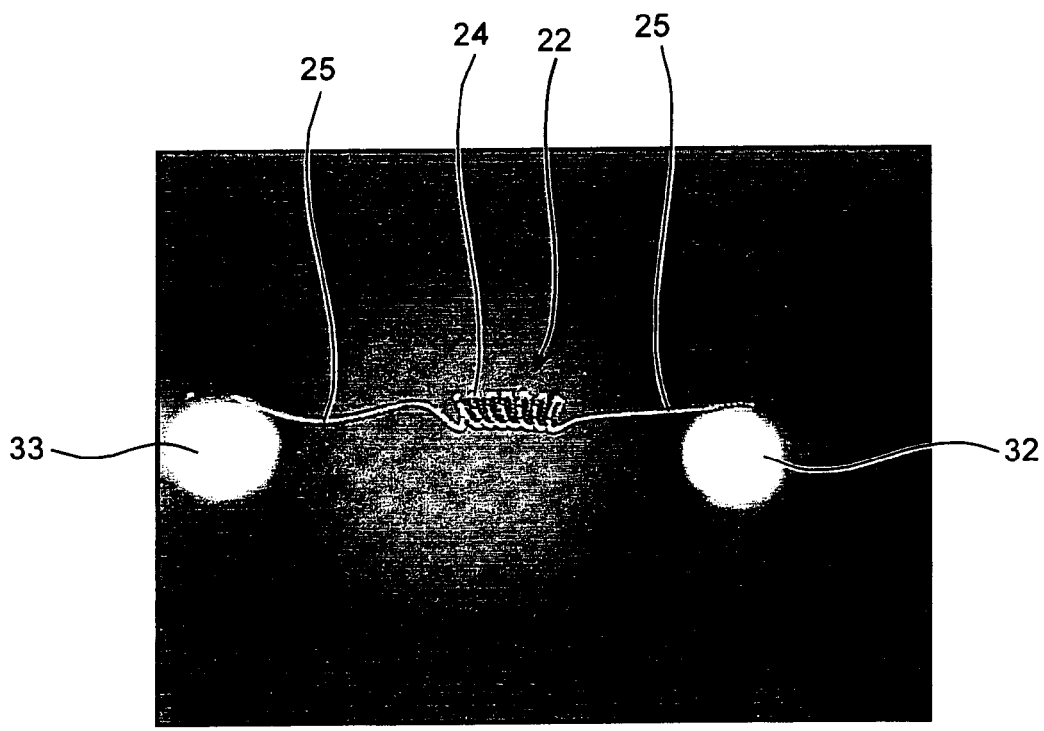
FIG. 17 is a photograph showing an entire shape of a heater coil of the comparative example.

FIGS. 14 and 17 show the entire shapes of the heater coils 22 respectively in the example and the comparative example. From FIG. 14, it can be seen that no distortion is present at all in the bead portion 24 of the heater coil 22 in the example. In contrast, it can be seen that, in the comparative example, the bead portion 24 of the heater coil 22 is distorted and adjacent wound portions of the bead portion 24 are almost contact each other. The cause of the distortion like this is that, when welding is performed without the primary core wire, the wound portions of the heater coil 22 is crushed due to carelessness or the coil shape is broken.

When the adjacent wound portions of the bead portion 24 contact each other or the coil is broken, the contact or broken portion is short-circuited. Therefore, the effective length that contributes to the resistance of the heater coil 22 is reduced, and therefore, the resistance value is reduced. Therefore, presence or absence of a local short circuit in the heater coil 22 can be grasped by measuring the resistance value between the electrode pins 32, 33. To confirm the presence or the absence of this short circuit, 10 samples were prepared respectively for the example and the comparative example described above and the resistance values were measured. The samples for the example and the comparative example respectively underwent the same steps as those for the measurement of the bonding strength described above. Table 7 shows the measurement result.

TABLE 7

| | Unit: Ω |
|---|---|
| Example (bonded with core wire) | Comparative example (bonded without core wire) |
| 11.5 | 9.1 |
| 11.2 | 11.0 |
| 11.1 | 10.5 |
| 11.2 | 10.9 |
| 11.6 | 11.0 |
| 11.0 | 11.2 |
| 11.3 | 9.6 |
| 11.2 | 10.2 |
| 11.4 | 11.5 |
| 11.5 | 10.8 |

TABLE 7-continued

| | Unit: Ω |
|---|---|
| | Example (bonded with core wire) | Comparative example (bonded without core wire) |
| Average Value | 11.3 | 10.5 |
| Maximum Value | 11.6 | 11.5 |
| Minimum Value | 11.0 | 9.1 |
| Standard Deviation | 0.2 | 0.7 |

The minimum value of the resistance values of 10 samples for the example was 11.0Ω and the maximum value thereof was 11.6Ω. The standard deviation thereof was 0.2. In contrast, the minimum value of the resistance values of 10 samples for the comparative example was 9.1Ω and the maximum value thereof was 11.5Ω. The standard deviation for the comparative example was 0.7 and the values were dispersed being shifted to smaller resistance values. Thus, it was confirmed that, when the welding was performed with the primary core wire remained as it is, the adjacent wound portions of the bead portion 24 can be prevented from contacting with each other and the coils can be prevented from being broken.

As described above, according to the embodiment, even when the size of the combusting portion of the detecting element 2 is approximately same as that of the conventional combusting portion, the effective length of the bead portion 24 that is buried in the combusting portion of the heater coil 22 is longer than that of the case where the bead portion 24 is constituted of the conventional single coil. Therefore, the resistance of the heater coil 22 becomes larger and, therefore, the gas sensitivity of the catalytic combustion gas sensor 5 becomes higher and the S/N ratio thereof is improved.

Furthermore, because the heater coil 22 receives more combustion heat and causes resistance variation more efficiently, the response speed of the catalytic combustion gas sensor 5 becomes higher. Because the size of the combusting portion may be almost same as that of the conventional combusting portion, the weight of the combusting portion is almost same as that of the conventional combusting portion. Therefore, improvement of the gas sensitivity and improvement of the response speed of the catalytic combustion gas sensor 5 can be facilitated without sacrificing the supporting ability of the detecting element 2 in the lead portions 25.

Moreover, because the resistance of the heater coil 22 becomes larger by thinning the raw wire of the heater coil 22, reduction of the power consumption can be facilitated. Because the lead portions 25 respectively have the same constitution as that of a coil spring, an impact applied externally is absorbed by the spring elasticity of the lead portions 25. Therefore, the impact transmitted to the combusting portion of the detecting element is alleviated, and therefore, detachment of the catalyst layer 23, etc., do not tend to occur and significant variation of the zero point caused by the impact can be suppressed.

Furthermore, the catalytic combustion gas sensor 5 that has the heater coil 22 that is constituted of a coiled coil and for which dispersion of the resistance values of the heater coils 22 is small and the bonding strength between the heater coil 22 and the electrode pins 32, 33 is high can be obtained. When the catalytic combustion gas sensor 5 is manufactured, handling of the heater coil 22 constituted of a coiled coil is easy.

In the above, the present invention is not limited to the embodiment described above and can be variously changed. For example, the method for welding and the conditions thereof, or the method for etching and the conditions thereof can be changed as appropriate. The various numeral values and materials, etc., are examples and are not limited thereto.

INDUSTRIAL APPLICABILITY

As described above, the gas sensor heater coil, the gas sensor detecting element, the catalytic combustion gas sensor, and the manufacturing method of the catalytic combustion gas sensor according to the present invention are useful for a gas leak detector for a domestic use or an industrial use, and are especially suitable for an apparatus that detects combustible gases used for a fuel battery.

What is claimed is:

1. A manufacturing method of a catalytic combustion gas sensor that detects presence of a combustible gas based on variation of an electrical characteristic value of a heater coil obtained when the characteristic value is varied by combustion heat generated by burning of a gas that the gas sensor has contacted, the manufacturing method comprising: a coil manufacturing step of manufacturing a heater coil of which at least both ends thereof respectively have been formed into a coil by being wound on a core wire; a welding step of welding coiled portions on both ends of the heater coil respectively to an electrode in a state in which the coiled portions are wound on a core wire; a core wire eliminating step of eliminating the core wire; and a sintered-body coating step of coating a portion of the heater coil with a sintered body, the portion from which the core wire is eliminated.

2. A manufacturing method of a catalytic combustion gas sensor that detects presence of a combustible gas based on variation of an electrical characteristic value of a heater coil obtained when the characteristic value is varied by combustion heat generated by burning of a gas that the gas sensor has contacted, the manufacturing method comprising: a coil manufacturing step of manufacturing a heater coil of which at least both ends thereof respectively have been formed into a coil by being wound on a core wire; a welding step of welding coiled portions on both ends of the heater coil respectively to an electrode in a state in which the coiled portions are wound on a core wire; a core wire eliminating step of eliminating the core wire except welded portions of the heater coil and the electrodes; and a sintered-body coating step of coating at least a part of a portion of the heater coil with a sintered body, the portion at which the core wire is not present.

3. The manufacturing method of a catalytic combustion gas sensor according to claim 1, wherein at the welding step, any one of a resistance welding method, a laser welding method, and a thermo-compression bonding method is performed while the ends wound on the core wire of the heater coil are kept pressed to the electrodes.

4. The manufacturing method of a catalytic combustion gas sensor according to claim 1, wherein the core wire is made from a metal material that is a more basic metal than the constituting material of the heater coil, and only the core wire is eliminated by etching at the core wire eliminating step.

5. The manufacturing method of a catalytic combustion gas sensor according to claim 1, wherein the core wire is made of nickel, the heater coil is made of platinum or platinum alloy, and the core wire is eliminated using an etching liquid for nickel at the core wire eliminating step.

6. The manufacturing method of a catalytic combustion gas sensor according to claim 1, wherein at the coil manufacturing step, at least a part of the portion of the heater coil covered with the sintered body is formed into a coiled coil that is formed by further winding a coiled wire into a coil, the coiled wire wound on the core wire.

7. The manufacturing method of a catalytic combustion gas sensor according to claim 1, wherein the core wire also acts as brazing material to bond the heater coil and the electrodes.

8. The manufacturing method of a catalytic combustion gas sensor according to claim 2, wherein at the welding step, any one of a resistance welding method, a laser welding method, and a thermo-compression bonding method is performed while the ends wound on the core wire of the heater coil are kept pressed to the electrodes.

9. The manufacturing method of a catalytic combustion gas sensor according to claim 2, wherein the core wire is made from a metal material that is more basic metal than the constituting material of the heater coil, and only the core wire is eliminated by etching at the core wire eliminating step.

10. The manufacturing method of a catalytic combustion gas sensor according to claim 2, wherein the core wire is made of nickel, the heater coil is made of platinum or platinum alloy, and the core wire is eliminated using an etching liquid for nickel at the core wire eliminating step.

11. The manufacturing method of a catalytic combustion gas sensor according to claim 2, wherein at the coil manufacturing step, at least a part of the portion of the heater coil covered with the sintered body is formed into a coiled coil that is formed by further winding a coiled wire into a coil, the coiled wire wound on the core wire.

12. The manufacturing method of a catalytic combustion gas sensor according to claim 2, wherein the core wire also acts as brazing material to bond the heater coil and the electrodes.

* * * * *